(12) United States Patent
Alcouffe

(10) Patent No.: US 9,572,799 B2
(45) Date of Patent: Feb. 21, 2017

(54) PYRAZOLOPYRIDINE DERIVATIVES FOR USE IN THE TREATMENT OF BLADDER CANCER

(71) Applicant: SANOFI, Paris (FR)

(72) Inventor: Chantal Alcouffe, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/897,929

(22) PCT Filed: Jun. 13, 2014

(86) PCT No.: PCT/EP2014/062456
§ 371 (c)(1),
(2) Date: Dec. 11, 2015

(87) PCT Pub. No.: WO2014/198942
PCT Pub. Date: Dec. 18, 2014

(65) Prior Publication Data
US 2016/0128989 A1    May 12, 2016

(30) Foreign Application Priority Data

Jun. 14, 2013  (FR) ..................... 13 55578

(51) Int. Cl.
| A61K 31/44 | (2006.01) |
| A61K 31/437 | (2006.01) |
| A61K 31/444 | (2006.01) |
| A61K 31/4545 | (2006.01) |
| A61K 31/5377 | (2006.01) |

(52) U.S. Cl.
CPC .......... *A61K 31/437* (2013.01); *A61K 31/444* (2013.01); *A61K 31/4545* (2013.01); *A61K 31/5377* (2013.01)

(58) Field of Classification Search
CPC .................................................... A61K 31/444
USPC ......................................................... 514/303
See application file for complete search history.

(56) References Cited

FOREIGN PATENT DOCUMENTS

| WO | WO-2010/059788 A1 | 5/2010 |
| WO | WO-2013/087744 A1 | 6/2013 |

OTHER PUBLICATIONS

Balicki, R. (1983). "Studies in the Field of Nitrogen Heterocyclic Compounds. Part XI. Abnormal Cyclocondensation of Ethyl 4,4,4-Trifluoroacetoacetate with Aminopyrazoles," *Polish Journal of Chemistry* 57:789-797.

(Continued)

*Primary Examiner* — Nizal Chandrakumar
(74) *Attorney, Agent, or Firm* — Morrison & Foerster LLP

(57) ABSTRACT

The invention relates to the use of compounds corresponding to formula (I), or a pharmaceutically acceptable salt thereof, for preparing a medicament for the treatment of bladder cancer.

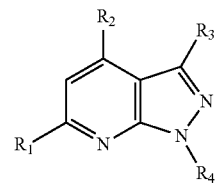

(I)

20 Claims, No Drawings

(56) References Cited

OTHER PUBLICATIONS

Chandak, N. et al. (Mar. 2013). "Exploration of Antimicrobial Potential of Pyrazolo [3,4-b]pyridine Scaffold Bearing Benzenesulfonamide and Trifluoromethyl Moieties," *Medicinal Chemistry Research* 22(11):5490-5503.

Di Martino, E. et al. (2009). "Mutant Fibroblast Growth Factor Receptor 3 Induces Intracellular Signaling and Cellular Transformation ina Cell Type- and Mutation-Specific Manner," *Oncogene* p. 1-11.

Dodurga, Y. et al. (2011). "Incidence of Fibroblast Growth Factor Receptor 3 Gene (FGFR3) A248C, S249C, G372C, and T375C Mutations in Bladder Cancer," *Genetics Mol. Res.* 10(1):86-95.

Gwynn, E.S. et al. (2006). "Bladder Cancer," *Curr. Opin. Oncol.* 18:277-283.

International Search Report mailed on Sep. 25, 2014, for PCT Application No. PCT/EP2014/062456, filed on Jun. 13, 2014, four pages.

Jemal, A. et al. (2005). "Cancer Statistics, 2005," *CA Cancer Journal for Clinicians* 55:10-30.

Knowles, M.A. et al. (2008). "Novel Therapeutic Targets in Bladder Cancer: Mutation and Expression of FGF Receptors," *Future Oncol.* 4(1):71-83.

Lamont, F.R. et al. (Jan. 4, 2011; e-pub. Nov. 30, 2010). "Small Molecule FGF Receptor Inhibitors Block FGFR-Dependent Urothelial Carcinoma Growth in vitro and in vivo," *British J. Cancer* 104(1):75-82.

National Cancer Institute (Jul. 1, 2015). Bladder Cancer Treatment (PDQ®), located at http://www.cancer.gov/cancertopics/pdq/treatment/bladder/Patient/page1>, last visited on Feb. 2, 2016, fifteen pages.

Oosterlink, W. et al. (2002). "Guidelines on Bladder Cancer," *European Urology* 41:105-112.

Otto, W. et al. (2009). "No Mutations of FGFR3 in Normal Urothelium in the Vicinity of Urothelial Carcinoma of the Bladder Harbouring Activating FGFR3 Mutations in Patients with Bladder Cancer," *Int. J. Cancer* 125:2205-2208.

Qing, J. et al. (May 2009). "Antibody-Based Targeting of FGFR3 in Bladder Carcinoma and t(4;14)-Positive Multiple Myeloma in Mice," *J. Clin. Investigation* 119(5):1216-1229.

Tomlinson, D.C. et al. (2007). "FGFR3 Protein Expression and its Relationship to Mutation Status and Prognostic Variables in Bladder Cancer," *J. Pathol.* 213(1):91-98.

Tomlinson, D.C. et al. (Aug. 30, 2007). "Knockdown by shRNA Identifies S249C Mutant FGFR3 as a Potential Therapeutic Target in Bladder Cancer," *Oncogene* 26(40):5889-5899.

Wu, X-R. et al. (Sep. 2005). "Urothelial Tumorigenesis: A Tale of Divergent Pathways," *Nature Reviews Cancer* 5:713-725.

PYRAZOLOPYRIDINE DERIVATIVES FOR USE IN THE TREATMENT OF BLADDER CANCER

CROSS REFERENCE TO RELATED APPLICATIONS

This application is a National Phase application under 35 U.S.C. §371 of International Application No. PCT/EP2014/062456 filed Jun. 13, 2014, which claims priority benefit to FR Application No. 1355578 filed Jun. 14, 2013, the disclosures of which are herein incorporated by reference in their entirety.

The present invention relates to the therapeutic use of pyrazolopyridine derivatives which are FGF (Fibroblast Growth Factor) receptor inhibitors, for preparing a medicament for the treatment of bladder cancer.

FGFs are a family of polypeptides synthesized by a large number of cells during embryonic development and by cells of adult tissues under various pathological conditions.

Bladder cancer is the sixth most common cancer in industrialized countries and the fourth in the United States, representing, in the latter country, more than 63 000 cases diagnosed every year and more than 13 000 deaths (Gwynn et al., 2006; Knowles et al., 2008; Jemal et al., 2005). These cancers affect mainly individuals over the age of 50, the population of which is greatly increasing. Throughout the world, at least 300 000 cases are detected each year, and this number is increasing. They are categorized in 2 main groups: i) superficial, papillary and non-invasive forms which do not penetrate the epithelium of the basal membrane or the underlying muscle (papilloma stages Ta and T1; Knowles et al., 2008) and represent between 70% and 80% of diagnosed cases, and ii) invasive forms (stages T2, T3 and T4; Knowles et al., 2008).

Although patients suffering from superficial and non-invasive bladder cancer have a good vital prognosis, this disease often presents multifocal carcinomas, which have a very high rate of recurrence (70%). Current treatment requires repeated and invasive procedures (transurethral resection combined with intravesical instillation of chemotherapy, such as mitomycin B, or an intravesical infusion of a solution of attenuated bacillus Calmette-Guerin (BCG)), each time requiring several days of hospitalization (http://www.cancer.gov/cancertopics/pdq/treatment/bladder/Patient/page1). All these characteristics make this disease extremely expensive by virtue of the medical follow-up that it requires. Furthermore, the current treatments are curative only for a minority of cases (less than 30%) and they cause numerous side-effects, such as pain during urination, nausea, fever, a considerable decrease in the time interval between urinations, bladder irritation, etc. (Oosterlink et al., 2002). Consequently, a curative treatment for bladder cancers while avoiding the numerous side-effects of the current medications is still a necessity.

Recently, a link has been demonstrated between these superficial urothelial cancers (UCs) of the bladder and the expression of a mutated form of FGF receptor 3 (FGF-R3). In this context, a very strong correlation has been made between the expression of mutated forms of FGF-R3 and low grade/stage bladder UCs. These mutations have also been identified in urothelial papillomas, and have been proposed as being responsible for the lesions that are a warning of papillary UCs (Knowles et al., 2008; Wu et al., 2005). The principal mutations are in the extracellular domain of FGF-R3 (75% of cases) at positions Arg248 and Ser249, in the transmembrane domain (25% of cases) at positions Gly372 and 382, Ser373, Tyr375 and Ala393 or else in the tyrosine kinase domain (2.5% of cases) at position Lys652 (Knowles et al., 2008; Dodurga et al., 2011). The two most common mutations are the replacement of Ser249 or of Tyr375 with a cysteine, leading to a ligand-independent constitutive dimerization of the receptor by virtue of an inter-chain disulphide bridge resulting in permanent activation of the receptor and of the underlying intracellular signalling pathways (di Martino et al., 2005; Qing et al., 2009). These "gain-of-function" mutations contribute to the proliferation of tumour cells, and to their ability to grow beyond confluence and to resist apoptosis (Tomlinson et al, 2007b; di Martino et al., 2009; Lamont et al., 2011). Furthermore, it appears that expression of the FGF-R3 protein correlates strongly with the presence of these mutations, with increased expression in the majority of superficial tumours carrying these FGF-R3 mutations (Tomlinson et al., 2007a), whereas these mutated forms are not detected in healthy urothelium (Otto et al., 2009).

The Ser249Cys mutation is the most common mutation in bladder UCs. It is present in more than 70% of the superficial forms of UCs. Reduction of the expression of this mutated form of FGF-R3 using an siRNA approach has made it possible to show that this mutated receptor controls the proliferation and growth of bladder cancer tumour cells independent of attachment to a substrate (Tomlinson et al., 2007b). This mutated form of FGF-R3 therefore appears to be a therapeutic target of choice for the treatment of superficial and non-invasive bladder cancers. The TCC97-7 cell line described in the literature is a relevant line for studying the effect of compounds for treating FGF receptor-3 Ser249Cys-mutation-dependent bladder cancers and the overexpression of this mutated receptor (Qing et al., 2009; Lamont et al., 2011). This line has therefore been used for evaluating the ability of the FGF-R antagonists of the present invention to counteract the pro-tumour effects of the Ser249Cys mutation of FGF receptor 3.

Thus, a subject of the present invention is the therapeutic use of the compound, which is a pyrazolopyridine derivative, corresponding to formula (I):

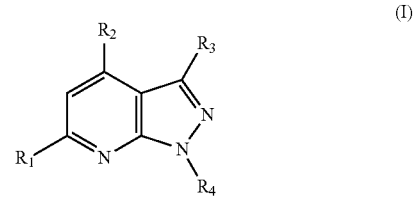

in which:
R$_1$ represents an aryl or heteroaryl group optionally substituted with one or more substituents chosen from:
a halogen atom,
a cyano group,
an —NR$_5$R$_5$' group where R$_5$ and R$_5$' are as defined below,
an —NR$_7$R$_8$ group such that R$_7$ and R$_8$ form, together with the nitrogen atom to which they are attached, a heterocycloalkyl comprising one or more heteroatoms chosen from a nitrogen atom or an oxygen atom,
a —COR$_{10}$ group where R$_{10}$ represents a hydroxyl group or an —NR$_5$R$_5$' group, where R$_5$ and R$_5$' are as defined below, a —CONR$_6$R$_6$' group where R$_6$ et R$_6$' form, together with the nitrogen atom to which they are attached, a heterocycloalkyl comprising one or more heteroatoms chosen from a nitrogen atom or an oxygen atom, an —NHSO$_2$CH$_3$ group, an —OR$_9$ group where R$_9$ represents a linear (C$_1$-C$_3$) alkyl group, or R$_1$ represents a bicyclic group of formula A below:

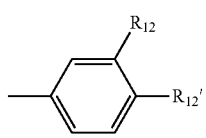

(A)

in which R$_{11}$ and R$_{11}$' form, together with the carbon atoms to which they are attached, a heterocycloalkyl comprising one or more heteroatoms chosen from a nitrogen atom and an oxygen atom, such that the group (A) advantageously forms a dihydrobenzimidazolonyl group, R$_2$ represents a haloalkyl group, R$_3$ represents:
  an aryl group, optionally substituted with one or more alkoxy groups,
  or
  a heteroaryl group, R$_4$ represents:
  a hydrogen atom,
  a linear (C$_1$-C$_3$)alkyl group, optionally substituted with a —NR$_5$R$_5$' group where R$_5$ and R$_5$' are as defined below, or an —NR$_6$R$_6$' group such that R$_6$ and R$_6$' form, together with the nitrogen atom to which they are attached, a heterocycloalkyl comprising one or more heteroatoms chosen from a nitrogen atom or an oxygen atom, R$_5$ and R$_5$', which may be identical or different, represent a hydrogen atom or a linear alkyl group, on the condition that the compound of formula (I) is other than (3-methoxyphenyl)-6-(4-methoxyphenyl)-1-methyl-4-(trifluoromethyl)pyrazolo[3,4-b]pyridine, or a pharmaceutically acceptable salt thereof, for preparing a medicament for the treatment of bladder cancer.

The compounds of formula (I) may exist in the form of bases or salified with acids or bases, in particular pharmaceutically acceptable acids or bases. Such addition salts form part of the invention.

These salts are advantageously prepared with pharmaceutically acceptable acids, but salts of other acids that are of use, for example, for purifying or isolating the compounds of formula (I) also form part of the invention.

In the context of the present invention, and unless otherwise mentioned in the text, the following will be understood:
  a halogen atom: a fluorine, chlorine, bromine or iodine atom;
  an alkyl group: a linear or branched, saturated aliphatic hydrocarbon-based group comprising from 1 to 4 carbon atoms. Examples that may be mentioned include methyl, ethyl, propyl, isopropyl, butyl, isobutyl groups, etc;
  a cycloalkyl group: a cyclic alkyl group, unless otherwise mentioned, having from 3 to 6 carbon atoms. Examples that may be mentioned include cyclopropyl, cyclobutyl, cyclopentyl, cyclohexyl groups, etc;
  an alkoxy group: a radical —O-alkyl in which the alkyl group is as defined previously. Examples that may be mentioned include —O—(C$_1$-C$_4$)alkyl or —(C$_1$-C$_4$)-alkoxy groups, and in particular as (i) —O—C$_1$alkyl group, the methoxy group, as (ii) —O—C$_2$alkyl group, the ethoxy group, as (iii) —O—C$_3$alkyl group, the propyloxy or —O-isopropyl group, and as (iv) —O—C$_4$alkyl group, the butoxy, —O-isobutyl or —O-tert-butyl group;
  a haloalkyl group: an alkyl group as defined above, in which all or some of the hydrogen atoms are replaced with halogen atoms, advantageously fluorine atoms;
  an aryl group: a cyclic aromatic group comprising between 6 and 8 carbon atoms, for example a phenyl group;
  heteroaryl: a cyclic aromatic group comprising between 3 and 10 atoms, including 1 or more heteroatoms, for example between 1 and 4 heteroatoms, such as nitrogen, oxygen or sulphur, this group comprising one ring. By way of examples, mention may be made of thienyl, pyridinyl, pyrazolyle imidazolyl, thiazolyl and triazolyl groups;
  a heterocycloalkyl: a monocyclic alkyl group comprising from 5 to 8 atoms, 1 or 2 of which are heteroatoms, such as oxygen or nitrogen. Mention may in particular be made of pyrrolodinyl, morpholinyl and piperidinyl groups.

In the present application, the terms "use of the compounds of formula (I) or a pharmaceutically acceptable salt thereof in the preparation of a medicament for the treatment of" can be understood to be synonymous with "compound of formula (I) or a pharmaceutically acceptable salt thereof for use in the treatment of".

A first subgroup which is a subject of the invention is the therapeutic use of the compound corresponding to formula (I) in which:

R$_1$ represents an aryl or heteroaryl group, advantageously a phenyl or pyridinyl group, optionally substituted with one or more substituents chosen from:
  a halogen atom, advantageously a fluorine atom,
  a cyano group,
  an —NR$_5$R$_5$' group where R$_5$ and R$_5$' are as defined below,
  an —NR$_7$R$_8$ group such that R$_7$ and R$_8$ form, together with the nitrogen atom to which they are attached, a heterocycloalkyl comprising one or more heteroatoms chosen from a nitrogen atom or an oxygen atom,
  a —COR$_{10}$ group where R$_{10}$ represents a hydroxyl group or an —NR$_5$R$_5$' group, where R$_5$ and R$_5$' are as defined below,
  a —CONR$_6$R$_6$' group where R$_6$ and R$_6$' form, together with the nitrogen atom to which they are attached, a heterocycloalkyl comprising one or more heteroatoms chosen from a nitrogen atom or an oxygen atom,
  an —NHSO$_2$CH$_3$ group,
  an —OR$_9$ group where R$_9$ represents a linear (C$_1$-C$_3$) alkyl group, or R$_1$ represents a bicyclic group of formula A below:

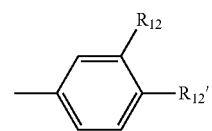

(A)

in which $R_{11}$ and $R_{11}'$ form, together with the carbon atoms to which they are attached, a heterocycloalkyl comprising one or more heteroatoms chosen from a nitrogen atom and an oxygen atom, such that the group (A) advantageously forms a dihydrobenzimidazolonyl group, $R_2$ represents a haloalkyl group advantageously chosen from:
 a —$CF_3$ group, or
 a —$CHF_2$ group, $R_3$ represents:
 an aryl group, advantageously a phenyl group, optionally substituted with one or more alkoxy groups, advantageously a methoxy group,
 or
 a heteroaryl group, advantageously a pyridinyl group, $R_4$ represents:
 a hydrogen atom,
 a linear ($C_1$-$C_3$)alkyl group, optionally substituted with an —$NR_5R_5'$ group where $R_5$ and $R_5'$ are as defined below, or an —$NR_6R_6'$ group such that $R_6$ and $R_6'$ form, together with the nitrogen atom to which they are attached, a heterocycloalkyl comprising one or more heteroatoms chosen from a nitrogen atom or an oxygen atom, $R_5$ and $R_5'$, which may be identical or different, represent a hydrogen atom or a linear alkyl group, on the condition that the compound of formula (I) is other than (3-methoxyphenyl)-6-(4-methoxyphenyl)-1-methyl-4-(trifluoromethyl)pyrazolo[3,4-b]pyridine, or a pharmaceutically acceptable salt thereof, for preparing a medicament for the treatment of bladder cancer.

A second subgroup which is a subject of the invention is the therapeutic use of the compound corresponding to formula (I) in which:

$R_1$ represents an aryl or heteroaryl group optionally substituted with one or more substituents chosen from:
 a halogen atom,
 a cyano group,
 an —$NR_5R_5'$ group where $R_5$ and $R_5'$ are as defined below,
 an —$NR_7R_8$ group such that $R_7$ and $R_8$ form, together with the nitrogen atom to which they are attached, a heterocycloalkyl comprising one or more heteroatoms chosen from a nitrogen atom or an oxygen atom,
 a —$CONR_5R_5'$ group, where $R_5$ and $R_5'$ are as defined below,
 a —$CONR_6R_6'$ group, where $R_6$ and $R_6'$ form, together with the nitrogen atom to which they are attached, a heterocycloalkyl comprising one or more heteroatoms chosen from a nitrogen atom or an oxygen atom,
 an —$OR_9$ group where $R_9$ represents a linear ($C_1$-$C_3$) alkyl group, $R_2$ represents a haloalkyl group, $R_3$ represents:
 an aryl group, optionally substituted with one or more alkoxy groups,
 or
 a heteroaryl group, $R_4$ represents:
 a hydrogen atom,
 a linear ($C_1$-$C_3$)alkyl group, optionally substituted with an —$NR_5R_5'$ group where $R_5$ and $R_5'$ are as defined below, or an —$NR_6R_6'$ group such that $R_6$ and $R_6'$ form, together with the nitrogen atom to which they are attached, a heterocycloalkyl comprising one or more heteroatoms chosen from a nitrogen atom or an oxygen atom, $R_5$ and $R_5'$, which may be identical or different, independently represent a hydrogen atom or a linear alkyl group, on the condition that the compound of formula (I) is other than 3-(3-methoxyphenyl)-6-(4-methoxyphenyl)-1-methyl-4-(trifluoromethyl)pyrazolo[3,4-b]pyridine, or a pharmaceutically acceptable salt thereof, for preparing a medicament for the treatment of bladder cancer.

A third subgroup which is a subject of the invention is the therapeutic use of the compound corresponding to formula (I) in which:

$R_1$ represents an aryl or heteroaryl group, advantageously a phenyl or pyridinyl group, optionally substituted with one or more substituents chosen from:
 a halogen atom, advantageously a fluorine atom,
 a cyano group,
 an —$NR_5R_5'$ group where $R_5$ and $R_5'$ are as defined below,
 an —$NR_7R_8$ group such that $R_7$ and $R_8$ form, together with the nitrogen atom to which they are attached, a heterocycloalkyl comprising one or more heteroatoms chosen from a nitrogen atom or an oxygen atom,
 a —$CONR_5R_5'$ group, where $R_5$ and $R_5'$ are as defined below,
 a —$CONR_6R_6'$ group where $R_6$ and $R_6'$ form, together with the nitrogen atom to which they are attached, a heterocycloalkyl comprising one or more heteroatoms chosen from a nitrogen atom or an oxygen atom,
 an —$OR_9$ group where $R_9$ represents a linear ($C_1$-$C_3$) alkyl group, $R_2$ represents a haloalkyl group advantageously chosen from:
 a —$CF_3$ group, or
 a —$CHF_2$ group, $R_3$ represents:
 an aryl group, advantageously a phenyl group, optionally substituted with one or more alkoxy groups,
 or
 a heteroaryl group, advantageously a pyridinyl group, $R_4$ represents:
 a hydrogen atom,
 a linear ($C_1$-$C_3$)alkyl group, optionally substituted with an —$NR_5R_5'$ group where $R_5$ and $R_5'$ are as defined below, or an —$NR_6R_6'$ group such that $R_6$ and $R_6'$ form, together with the nitrogen atom to which they are attached, a heterocycloalkyl comprising one or more heteroatoms chosen from a nitrogen atom or an oxygen atom, $R_5$ and $R_5'$, which may be identical or different, independently represent a hydrogen atom or a linear alkyl group, on the condition that the compound of formula (I) is other than 3-(3-methoxyphenyl)-6-(4-methoxyphenyl)-1-methyl-4-(trifluoromethyl)pyrazolo[3,4-b]pyridine, or a pharmaceutically acceptable salt thereof, for preparing a medicament for the treatment of bladder cancer.

A fourth subgroup which is a subject of the invention is the therapeutic use of the compound corresponding to formula (I) in which:

$R_2$ represents a haloalkyl group advantageously chosen from:
  a —$CF_3$ group, or
  a —$CHF_2$ group,
on the condition that the compound of formula (I) is other than 3-(3-methoxyphenyl)-6-(4-methoxyphenyl)-1-methyl-4-(trifluoromethyl)pyrazolo[3,4-b]pyridine,
or a pharmaceutically acceptable salt thereof, for preparing a medicament for the treatment of bladder cancer.

A fifth subgroup which is a subject of the invention is the therapeutic use of the compound corresponding to formula (I) in which:
  $R_1$ represents a phenyl or pyridinyl group optionally substituted with one or more substituents chosen from:
    a fluorine atom,
    a cyano group,
    an —$NR_5R_5'$ group where $R_5$ and $R_5'$ are as defined below,
    an —$NR_7R_8$ group such that $R_7$ and $R_8$ form, together with the nitrogen atom to which they are attached, a heterocycloalkyl comprising one or more heteroatoms chosen from a nitrogen atom or an oxygen atom,
    a —$COR_{10}$ group where $R_{10}$ represents a hydroxyl group or an —$NR_5R_5'$ group, where $R_5$ and $R_5'$ are as defined below,
    a —$CONR_6R_6'$ group where $R_6$ and $R_6'$ form, together with the nitrogen atom to which they are attached, a heterocycloalkyl comprising one or more heteroatoms chosen from a nitrogen atom or an oxygen atom,
    an —$NHSO_2CH_3$ group,
    an —$OR_9$ group where $R_9$ represents a methyl group,
  or $R_1$ represents a bicyclic group of formula A below:

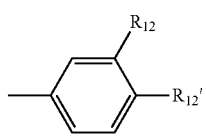

(A)

in which $R_{11}$ and $R_{11}'$ form, together with the carbon atoms to which they are attached, a heterocycloalkyl comprising one or more heteroatoms chosen from a nitrogen atom and an oxygen atom, such that the group (A) advantageously forms a dihydrobenzimidazolonyl group,
  $R_2$ represents a group:
    —$CF_3$, or
    —$CHF_2$,
  $R_3$ represents:
    an aryl group, optionally substituted with a methoxy group,
    or
    a pyridinyl group,
  $R_4$ represents:
    a hydrogen atom,
    a linear ($C_1$-$C_2$)alkyl group, optionally substituted with an —$NR_5R_5'$ group where $R_5$ and $R_5'$ are as defined below, or an —$NR_6R_6'$ group such that $R_6$ and $R_6'$ form, together with the nitrogen atom to which they are attached, a heterocycloalkyl comprising one or more heteroatoms chosen from a nitrogen atom or an oxygen atom,
  $R_5$ and $R_5'$, which may be identical or different, independently represent a hydrogen atom or a linear ($C_1$-$C_3$) alkyl group,
on the condition that the compound of formula (I) is other than 3-(3-methoxyphenyl)-6-(4-methoxyphenyl)-1-methyl-4-(trifluoromethyl)pyrazolo[3,4-b]pyridine,
or a pharmaceutically acceptable salt thereof, for preparing a medicament for the treatment of bladder cancer.

A sixth subgroup which is a subject of the invention is the therapeutic use of the compound corresponding to formula (I) in which:
  $R_1$ represents a phenyl or pyridinyl group optionally substituted with one or more substituents chosen from:
    a fluorine atom,
    a cyano group,
    an —$NR_5R_5'$ group where $R_5$ and $R_5'$ are as defined below,
    an —$NR_7R_8$ group such that $R_7$ and $R_8$ form, together with the nitrogen atom to which they are attached, a heterocycloalkyl comprising one or more heteroatoms chosen from a nitrogen atom or an oxygen atom,
    a —$CONR_5R_5'$ group, where $R_5$ and $R_5'$ are as defined below,
    a —$CONR_6R_6'$ group where $R_6$ and $R_6'$ form, together with the nitrogen atom to which they are attached, a heterocycloalkyl comprising one or more heteroatoms chosen from a nitrogen atom or an oxygen atom,
    an —$OR_9$ group where $R_9$ represents a methyl group,
  $R_2$ represents a group:
    a —$CF_3$, or
    —$CHF_2$,
  $R_3$ represents:
    an aryl group, optionally substituted with a methoxy group,
    or
    a pyridinyl group,
  $R_4$ represents:
    a hydrogen atom,
    a linear ($C_1$-$C_2$)alkyl group, optionally substituted with an —$NR_5R_5'$ group where $R_5$ and $R_5'$ are as defined below, or an —$NR_6R_6'$ group such that $R_6$ and $R_6'$ form, together with the nitrogen atom to which they are attached, a heterocycloalkyl comprising one or more heteroatoms chosen from a nitrogen atom or an oxygen atom,
  $R_5$ and $R_5'$, which may be identical or different, independently represent a hydrogen atom or a linear ($C_1$-$C_3$) alkyl group,
on the condition that the compound of formula (I) is other than 3-(3-methoxyphenyl)-6-(4-methoxyphenyl)-1-methyl-4-(trifluoromethyl)pyrazolo[3,4-b]pyridine,
or a pharmaceutically acceptable salt thereof, for preparing a medicament for the treatment of bladder cancer.

A seventh subgroup which is a subject of the invention is the therapeutic use of the compound corresponding to formula (I) in which:
  $R_1$ represents a phenyl group optionally substituted with one or more substituents chosen from:
    a halogen atom, advantageously a fluorine atom,
    a cyano group,
    an —$NR_5R_5'$ group where $R_5$ and $R_5'$ are as defined below,
    an —$NR_7R_8$ group such that $R_7$ and $R_8$ form, together with the nitrogen atom to which they are attached, a heterocycloalkyl, a —COR₁₀ group where R₁₀ represents a hydroxyl group or an —NR₅R₅' group, where R₅ and R₅' are as defined below;

a —CONR₆R₆' group where R₆ and R₆' form, together with the nitrogen atom to which they are attached, a heterocycloalkyl comprising one or more heteroatoms chosen from a nitrogen atom or an oxygen atom, an —NHSO₂CH₃ group, an —OR₉ group where R₉ represents a methyl group, or R₁ represents a bicyclic group of formula A below:

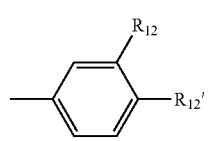

(A)

in which R₁₁ and R₁₁' form, together with the carbon atoms to which they are attached, a heterocycloalkyl comprising one or more heteroatoms chosen from a nitrogen atom and an oxygen atom, such that the group (A) advantageously forms a dihydrobenzimidazolonyl group, R₅ and R₅', which may be identical or different, independently represent a hydrogen atom or a linear (C₁-C₃) alkyl group, on the condition that the compound of formula (I) is other than 3-(3-methoxyphenyl)-6-(4-methoxyphenyl)-1-methyl-4-(trifluoromethyl)pyrazolo[3,4-b]pyridine, or a pharmaceutically acceptable salt thereof, for preparing a medicament for the treatment of bladder cancer.

An eighth subgroup which is a subject of the invention is the therapeutic use of the compound corresponding to formula (I) in which:

R₁ represents a phenyl group optionally substituted with one or more substituents chosen from:
a halogen atom, advantageously a fluorine atom,
a cyano group,
an —NR₅R₅' group where R₅ and R₅' are as defined below,
an —NR₇R₈ group such that R₇ and R₈ form, together with the nitrogen atom to which they are attached, a heterocycloalkyl comprising one or more heteroatoms chosen from a nitrogen atom or an oxygen atom,
a —CONR₅R₅' group, where R₅ and R₅' are as defined below,
a —CONR₆R₆' group where R₆ and R₆' form, together with the nitrogen atom to which they are attached, a heterocycloalkyl comprising one or more heteroatoms chosen from a nitrogen atom or an oxygen atom,
an —OR₉ group where R₉ represents a linear (C₁-C₃) alkyl group,
R₅ and R₅', which may be identical or different, independently represent a hydrogen atom or a linear (C₁-C₃) alkyl group, on the condition that the compound of formula (I) is other than 3-(3-methoxyphenyl)-6-(4-methoxyphenyl)-1-methyl-4-(trifluoromethyl)pyrazolo[3,4-b]pyridine, or a pharmaceutically acceptable salt thereof, for preparing a medicament for the treatment of bladder cancer.

A ninth subgroup which is a subject of the invention is the therapeutic use of the compound corresponding to formula (I) in which:

R₁ represents a pyridinyl group optionally substituted with one or more substituents chosen from:
a cyano group,
an —OR₉ group where R₉ represents a linear (C₁-C₃) alkyl group,
or a pharmaceutically acceptable salt thereof, for preparing a medicament for the treatment of bladder cancer.

A tenth subgroup which is a subject of the invention is the therapeutic use of the compound corresponding to formula (I) in which R₄ represents a hydrogen atom, or a pharmaceutically acceptable salt thereof, for preparing a medicament for the treatment of bladder cancer.

An eleventh subgroup which is a subject of the invention is the therapeutic use of the compound corresponding to formula (I) in which:

R₄ represents:
a linear (C₁-C₃)alkyl group, optionally substituted with an —NR₅R₅' group where R₅ and R₅' are as defined below, or an —NR₆R₆' group such that R₆ and R₆' form, together with the nitrogen atom to which they are attached, a heterocycloalkyl comprising one or more heteroatoms chosen from a nitrogen atom or an oxygen atom,
R₅ and R₅', which may be identical or different, independently represent a hydrogen atom or a linear alkyl group, or a pharmaceutically acceptable salt thereof, for preparing a medicament for the treatment of bladder cancer.

The subgroups defined above, taken separately or in combination, also form part of the invention.

As compounds of general formula (I) for therapeutic use, mention may in particular be made of:

Compound 1. 3-(1-methyl-3-phenyl-4-trifluoromethyl-1H-pyrazolo[3,4-b]pyridin-6-yl)benzamide, Compound 2. 2-Fluoro-N-methyl-5-(1-methyl-3-phenyl-4-trifluoromethyl-1H-pyrazolo[3,4-b]pyridin-6-yl)benzamide, Compound 3. Dimethyl-[3-(1-methyl-3-phenyl-4-trifluoromethyl-1H-pyrazolo[3,4-b]pyridin-6-yl)phenyl]amine, Compound 4. N,N-Dimethyl-3-(1-methyl-3-phenyl-4-trifluoromethyl-1H-pyrazolo[3,4-b]pyridin-6-yl)benzamide, Compound 5. [4-(4-Difluoromethyl-3-phenyl-1H-pyrazolo[3,4-b]pyridin-6-yl)phenyl]pyrrolidin-1-ylmethanone hydrochloride, Compound 6. [3-(4-Difluoromethyl-3-phenyl-1H-pyrazolo[3,4-b]pyridin-6-yl)phenyl]pyrrolidin-1-ylmethanone hydrochloride, Compound 7. 4-Difluoromethyl-3-phenyl-6-(3-piperidin-1-ylphenyl)-1H-pyrazolo[3,4-b]pyridine hydrochloride, Compound 8. 2-Amino-5-[1-(2-dimethylamino-ethyl)-3-phenyl-4-trifluoromethyl-1H-pyrazolo[3,4-b]pyridin-6-yl]benzonitrile, Compound 9. 2-Methoxy-5-(1-methyl-3-phenyl-4-trifluoromethyl-1H-pyrazolo[3,4-b]pyridin-6-yl)nicotinonitrile, Compound 10. 2-Amino-5-[3-phenyl-1-(2-piperidin-1-yl-ethyl)-4-trifluoromethyl-1H-pyrazolo[3,4-b]pyridin-6-yl]benzonitrile, Compound 11. 2-Amino-5-(4-difluoromethyl-3-pyridin-3-yl-1H-pyrazolo[3,4-b]pyridin-6-yl)benzonitrile, Compound 12. 2-Amino-5-[4-difluoromethyl-3-(3-methoxyphenyl)-1H-pyrazolo[3,4-b]pyridin-6-yl]benzonitrile, Compound 13. N-[3-(3-Phenyl-4-trifluoromethyl-1H-pyrazolo[3,4-b]pyridin-6-yl)phenyl]methanesulphonamide hydrochloride, Compound 14. 2-Amino-5-[4-difluoromethyl-1-(2-dimethylaminoethyl)-3-phenyl-1H-pyrazolo[3,4-b]pyridin-6-yl]benzonitrile,
Compound 15. 5-(3-Phenyl-4-trifluoromethyl-1H-pyrazolo[3,4-b]pyridin-6-yl)-1,3-dihydrobenzoimidazol-2-one,
Compound 16. 4-(3-Phenyl-4-trifluoromethyl-1H-pyrazolo[3,4-b]pyridin-6-yl)phenylamine,
Compound 17. N-Methyl-3-(3-phenyl-4-trifluoromethyl-1H-pyrazolo[3,4-b]pyridin-6-yl)benzamide hydrochloride,
Compound 18. 6-(4-Methoxyphenyl)-3-phenyl-4-trifluoromethyl-1H-pyrazolo[3,4-b]pyridine,
Compound 19. Dimethyl-[4-(3-phenyl-4-trifluoromethyl-1H-pyrazolo[3,4-b]pyridin-6-yl)phenyl]amine,
Compound 20. 2-Fluoro-5-(3-phenyl-4-trifluoromethyl-1H-pyrazolo[3,4-b]pyridin-6-yl)benzonitrile,
Compound 21. N-[3-(1-Methyl-3-phenyl-4-trifluoromethyl-1H-pyrazolo[3,4-b]pyridin-6-yl)phenyl]methanesulphonamide,
Compound 22. 2-Amino-5-(4-difluoromethyl-3-phenyl-1H-pyrazolo[3,4-b]pyridin-6-yl)benzonitrile hydrochloride,
Compound 23. 4-(1-Methyl-3-phenyl-4-trifluoromethyl-1H-pyrazolo[3,4-b]pyridin-6-yl)benzoic acid,
Compound 24. 6-(4-Morpholin-4-ylphenyl)-3-phenyl-4-trifluoromethyl-1H-pyrazolo[3,4-b]pyridine hydrochloride,
or a pharmaceutically acceptable salt thereof, for preparing a medicament for the treatment of bladder cancer.

It should be noted that the compounds above were named using IUPAC nomenclature by means of the ACDLABS 10.0 ACD/name (Advanced Chemistry development) or AutoNom (Beilstein Informations system) software.

In the text hereinbelow, the term "protective group (P)" is intended to mean a group that can, firstly, protect a reactive function such as a hydroxyl or an amine during a synthesis and, secondly, regenerate the intact reactive function at the end of the synthesis. Examples of protecting groups and also of protection and deprotection methods are given in *Protective Groups in Organic Synthesis*, Greene et al., 3rd Edition (John Wiley & Sons, Inc., New York).

The compounds of general formula (I) can be prepared according to the processes hereinafter.

The compound of formula (IV) when $R_2$ represents a —$CF_3$ group is obtained by methods known in the literature, starting from the 2-aminopyrazole (III) and the ethyl 4,4,4-trifluoro-3-oxobutanoate (II), according to the following reaction scheme, described in *Polish Journal of Chemistry*, 1983, 57, 789.

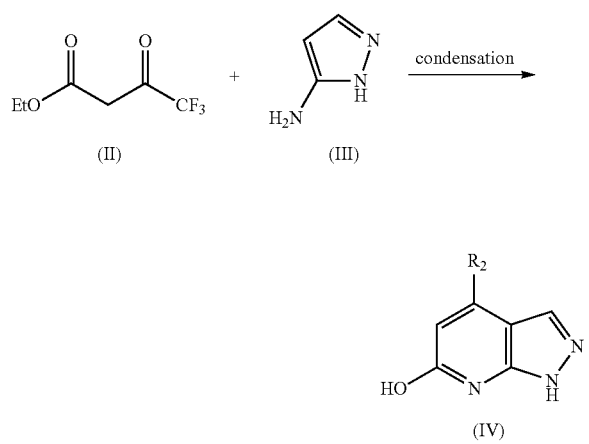

The compound of formula (IV) when $R_2$ represents a —$CHF_2$ group is obtained by a method similar to that described previously by condensation of the 2-aminopyrazole (III) and ethyl 4,4-difluoro-3-oxobutanoate.

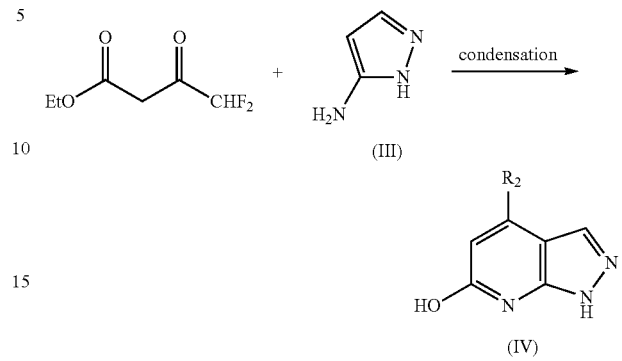

The compound of formula (XII) in which $R_2$ represents a —$CHF_2$ or —$CF_3$ group is obtained by chlorination, in the presence of $POCl_3$, of the compound of formula (IV) in which $R_2$ represents a —$CHF_2$ group or a —$CF_3$.

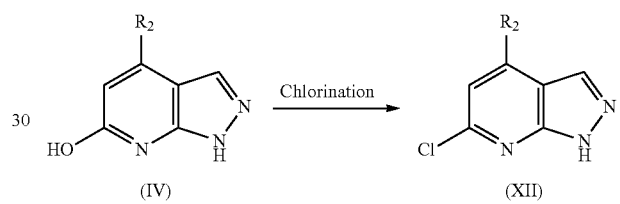

The compound of formula (VI) in which $R_2$ represents a —$CF_3$ group and $R_3$ a phenyl is obtained by methods known in the literature, starting from the 3-phenyl-1H-pyrazol-5-amine (V) and ethyl 4,4,4-trifluoro-3-oxobutanoate, according to the following reaction scheme, described in *Polish Journal of Chemistry*, 1983, 57, 789.

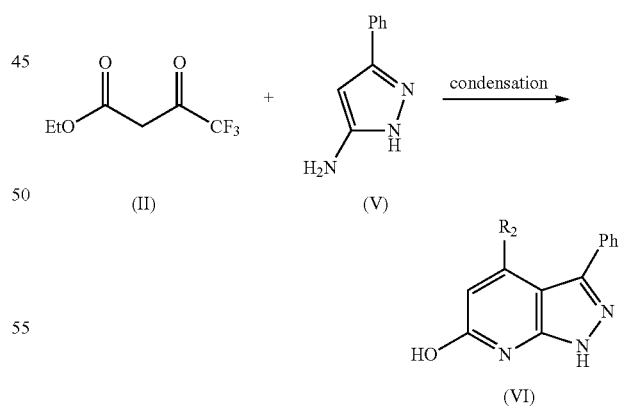

The compound of formula (VI) in which $R_2$ represents a —$CHF_2$ group is obtained by a method similar to that described previously starting from the 3-phenyl-1H-pyrazol-5-amine (V) and ethyl 4,4-difluoro-3-oxobutanoate.

Scheme 1 presents a pathway for obtaining the compounds of formula (I) in which $R_1$ is as defined previously, and $R_2$ represents a —$CF_3$ or —$CHF_2$ group.

Scheme 1 (Method 1):

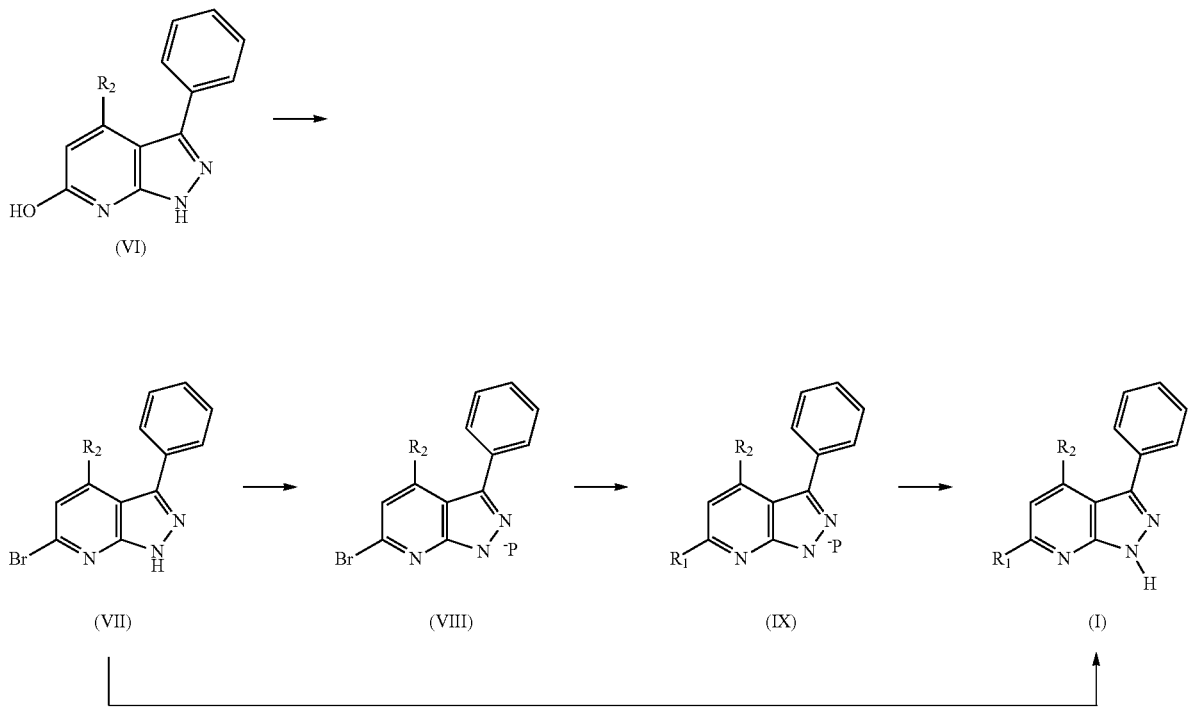

The compound of formula (VI) is subjected to a bromination reaction in the presence of POBr$_3$ in order to obtain the compound of formula (VII). The compound of formula (VII) is subjected to an alkylation reaction in the presence of a protective group P (such as tetrahydropyran) in order to obtain the compound of formula (VIII). The compound of formula (VIII) is subjected, in the presence of a palladium catalyst (such as tetrakis(triphenylphosphine)palladium), of a ligand (such as triphenylphosphine) and of a base (such as potassium phosphate dihydrate), to a reaction with phenylboronic or heteroarylboronic derivatives or phenylboronate esters or heteroarylboronate esters according to a Suzuki coupling, in order to obtain the compound of formula (IX). The compound of formula (IX) is subjected to a deprotection reaction in an acidic medium (such as hydrochloric acid or trifluoroacetic acid) in order to obtain the compounds of formula (I) in which R$_1$ is as defined previously, and R$_2$ represents a —CF$_3$ or —CHF$_2$ group.

The compound of formula (VII) may optionally be subjected, in the presence of a palladium catalyst (such as tetrakis(triphenylphosphine)palladium), of a ligand (such as triphenylphosphine) and of a base (such as potassium phosphate dihydrate), to a reaction with phenylboronic or heteroarylboronic derivatives or phenylboronate esters or heteroarylboronate esters according to a Suzuki coupling, in order to obtain the compound of formula (I) in which R$_1$ is as defined previously, and R$_2$ represents a —CF$_3$ or —CHF$_2$ group.

Scheme 2 presents a pathway for obtaining the compounds of formula (I) in which R$_1$ and R$_4$ are as defined previously except for a hydrogen atom.

Scheme 2 (Method 2):

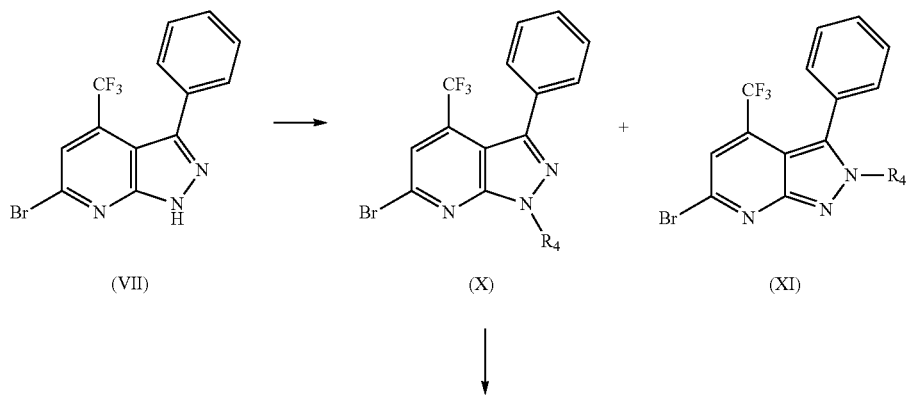

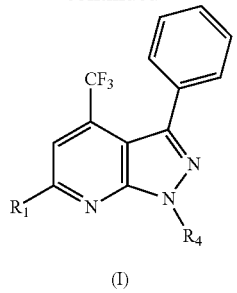

(I)

The compound of formula (VII) is subjected to an alkylation reaction in the presence of a base (such as caesium carbonate or potassium carbonate) and of a halogenated derivative R₄—X in order to obtain the compounds of formulae (X) and (XI). The compound of formula (X) is subjected, in the presence of a palladium catalyst (such as tetrakis(triphenylphosphine)palladium), of a ligand (such as triphenylphosphine) and of a base (such as potassium phosphate dihydrate), to a reaction with phenylboronic or heteroarylboronic derivatives or phenylboronate esters or heteroarylboronate esters according to a Suzuki coupling, in order to obtain the compounds of formula (I) in which $R_1$ and $R_4$ are as defined previously.

Scheme 3 presents a pathway for obtaining the compounds of formula (I) in which $R_2$ represents a —CHF₂ or —CF₃ group, and $R_1$, $R_3$ and $R_4$ are as defined previously with the exception of a hydrogen atom.

and of a base (such as caesium carbonate or potassium carbonate) in order to obtain the compounds of formulae (XIV) and (XV). The compound of formula (XIV) is subjected, in the presence of a palladium catalyst (such as tetrakis(triphenylphosphine)palladium), of a ligand (such as triphenylphosphine) and of a base (such as potassium phosphate dihydrate), to a reaction with phenylboronic or heteroarylboronic derivatives or phenylboronate esters or heteroarylboronate esters according to a Suzuki coupling, in order to obtain the compounds of formula (XVI). The compound of formula (XVI) is subjected, in the presence of a palladium catalyst (such as tetrakis(triphenylphosphine) palladium), of a ligand (such as triphenylphosphine) and of a base (such as potassium phosphate dihydrate), to a reaction with phenylboronic or heteroarylboronic derivatives or phenylboronate esters or heteroarylboronate esters according to a Suzuki coupling, in order to obtain the compound of Scheme 3 (Method 3):

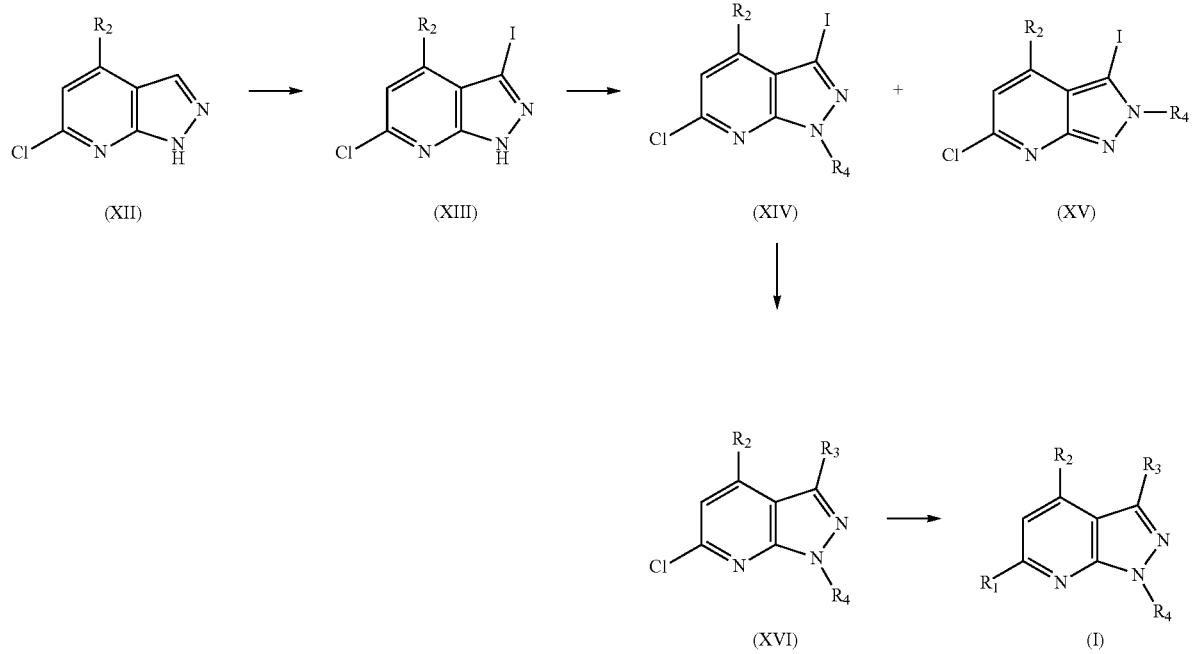

The compound of formula (XII) is subjected to an iodination reaction in the presence of N-iodosuccinimide in order to obtain the compound of formula (XIII). The compound of formula (XIII) is then subjected to an alkylation reaction in the presence of a halogenated derivative R₄—X formula (I) in which $R_2$ represents a —CHF₂ or —CF₃ group, and $R_1$, $R_3$ and $R_4$ are as defined previously with the exception of a hydrogen atom.

Scheme 4 presents a pathway for obtaining the compounds of formula (I) in which $R_2$ represents a —CHF₂ or —CF₃ group, and R₁ and R₃ are as defined previously with the exception of a hydrogen atom.

Scheme 4 (Method 4):

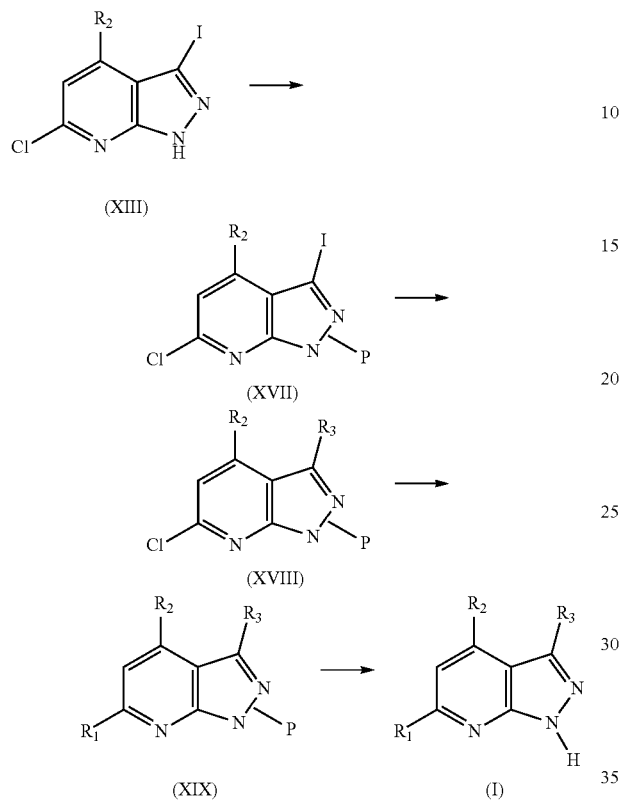

The compound of formula (XIII) is subjected to an alkylation reaction in the presence of a protective group P (such as tetrahydropyran) in order to obtain the compound of formula (XVII). The compound of formula (XVII) is subjected, in the presence of a palladium catalyst (such as tetrakis(triphenylphosphine)palladium), of a ligand (such as triphenylphosphine) and of a base (such as potassium phosphate dihydrate), to a reaction with phenylboronic or heteroarylboronic derivatives or phenylboronate esters or heteroarylboronate esters according to a Suzuki coupling, in order to obtain the compound of formula (XVIII). The compound of formula (XVIII) is subjected, in the presence of a palladium catalyst (such as tetrakis(triphenylphosphine) palladium), of a ligand and of a base (such as potassium phosphate dihydrate), to a reaction with phenylboronic or heteroarylboronic derivatives or phenylboronate esters or heteroarylboronate esters according to a Suzuki coupling, in order to obtain the compound of formula (XIX). The compound of formula (XIX) is then subjected to a deprotection reaction in an acidic medium (such as hydrochloric acid or trifluoroacetic acid) in order to obtain the compound of formula (I) in which R₂ represents a —CHF₂ or —CF₃ group, and R₁ and R₃ are as defined previously with the exception of a hydrogen atom.

In the schemes above, the starting compounds, the reactants and the intermediates, when their method of preparation is not described, are commercially available or described in the literature, or else can be prepared according to methods which are described therein or which are known to those skilled in the art.

According to another of its aspects, a subject of the invention is also the compounds of formulae (II) to (XIX) defined above. These compounds are useful as intermediates for synthesizing the compounds of formula (I).

The following abbreviations and molecular formulae are used:
AcOH: acetic acid
PTSA: para-toluenesulphonic acid
DME: Ethylene glycol dimethyl ether
DMF: N,N-dimethylformamide
DMSO: dimethyl sulphoxide
TBAF: tetrabutylammonium fluoride
TFA: trifluoroacetic acid
THF: Tetrahydrofuran
In the examples which follow:
The NMR analyses were carried out on Bruker Avance 250 MHz, 300 MHz, 400 MHz and 600 MHz apparatuses. The proton magnetic resonance (¹H NMR) spectra, as described below, are recorded at 400 MHz or 600 MHz in DMSO-d₆, using the DMSO-d₆ peak as a reference. The chemical shifts δ are expressed in parts per million (ppm). The signals observed are expressed in the following way: s=singlet; d=doublet; t=triplet; bs=broad singlet or unresolved peak; H=proton (for the rotamers, H$_M$ and H$_m$ are used to denote the major or minor isomers M and m respectively).
The melting points were measured on a Buchi B-545 apparatus.
The mass spectrometry analyses were carried out on an Alliance 2695 apparatus (UV: PDA 996, MS: ZQ (simple Quad) ZQ2), Waters UPLC Acquity (UV: Acquity PDA, MS: SQD (simple Quad) SQW).

EXAMPLE 1

Compound 3

N,N-dimethyl-3-[1-methyl-3-phenyl-4-(trifluoromethyl)-1H-pyrazolo[3,4-b]pyridin-6-yl]aniline 3-phenyl-4-(trifluoromethyl)-1H-pyrazolo[3,4-b]pyridin-6-ol 2 g (12.5 mmol) of 3-phenyl-1H-pyrazol-5-amine were added to 2.1 g (11.4 mmol) of ethyl 4,4,4-trifluoro-3-oxobutanoate in 16 ml of a 1/1 mixture of AcOH/H₂O. The reaction medium was heated at 90° C. for 18 hours and then cooled. The precipitate obtained was filtered off, washed with an aqueous 20% acetic acid solution and then dried under reduced pressure at 50° C. for 18 hours. 2.5 g of a solid were obtained.
MH+: 280

6-bromo-3-phenyl-4-(trifluoromethyl)-1H-pyrazolo[3,4-b]pyridine 3.1 g (10.8 mmol) of POBr₃ were added to 1 g (3.8 mmol) of 3-phenyl-4-(trifluoromethyl)-1H-pyrazolo[3,4-b]pyridin-6-ol in 20 ml of toluene. The reaction medium was heated at 90° C. for 18 hours. The reaction medium was concentrated under reduced pressure and then purified by silica gel column chromatography, elution being carried out with a 4/1 hexane/ethyl acetate mixture. 338 mg of a solid were obtained.
MH+=306

6-bromo-1-methyl-3-phenyl-4-(trifluoromethyl)-1H-pyrazolo[3,4-b]pyridine 2.18 ml (35 mmol) of methyl iodide and 4.8 g (35.08 mmol) of potassium carbonate were added, at ambient temperature, to 10 g (29 mmol) of 6-bromo-3-phenyl-4-(trifluoromethyl)-1H-pyrazolo[3,4-b]pyridine, in 200 ml of anhydrous DMF, under an inert nitrogen atmosphere. The reaction medium was stirred for 2 hours and then hydrolyzed with water. The aqueous phase was extracted with ethyl acetate. The organic phase obtained was washed with water, dried over sodium sulphate and then concentrated under reduced pressure. The colourless oil obtained was purified by silica gel column chromatography, elution being carried out with a heptane/dichloromethane mixture. 7.03 g of a colourless oil were obtained.

MH+=356

N,N-dimethyl-3-[1-methyl-3-phenyl-4-(trifluoromethyl)-1H-pyrazolo[3,4-b]pyridin-6-yl]aniline 0.111 g (0.67 mmol) of [3-(dimethylamino)phenyl]boronic acid, 0.418 g (1.68 mmol) of potassium phosphate dihydrate and 13 mg (0.01 mmol) of tetrakis(triphenylphosphine)palladium were added to 200 mg (0.56 mmol) of 6-bromo-1-methyl-3-phenyl-4-(trifluoromethyl)-1H-pyrazolo[3,4-b]pyridine in 3 ml of a DME/H$_2$O mixture (1/1) under an inert argon atmosphere. The reaction medium was microwave-heated at 150° C. for 15 minutes and then hydrolyzed with water and extracted with ethyl acetate. The organic phase was dried over sodium sulphate and then concentrated under reduced pressure. The residue obtained was purified by silica gel column chromatography, elution being carried out with a heptane/dichloromethane mixture. 157 mg of a white solid were obtained.

MH+: 396

Melting point: 95° C.

$^1$H NMR (400 MHz, DMSO-d$_6$) δ ppm: 8.10 (s, 1H) 7.61 (d, J=2.3 Hz, 1H) 7.58 (d, J=7.8 Hz, 1H) 7.46-7.55 (bs, 5H) 7.39 (t, J=7.8 Hz, 1H) 6.93 (dd, J=8.2 Hz, 2.3 Hz, 1H) 4.24 (s, 3H) 3.03 (s, 6H)

EXAMPLE 2

Compound 5

{4-[4-(difluoromethyl)-3-phenyl-1H-pyrazolo[3,4-b]pyridin-6-yl]phenyl}(pyrrolidin-1-yl)methanone

6-chloro-4-(difluoromethyl)-1H-pyrazolo[3,4-b]pyridine 10 g (60.2 mmol) of ethyl 4,4-difluoro-3-oxobutanoate were added to 5 g (60.2 mmol) of 3-aminopyrazole in a mixture of acetic acid/H$_2$O. The reaction medium was heated at 85° C. for 8 hours. After a return to ambient temperature, the precipitate obtained was filtered off, washed with water, and then dried under reduced pressure. 7.2 g of a solid were obtained, which was taken up in 28.7 g (187.1 mmol) of POCl$_3$. The reaction medium was heated at 85° C. for 4 hours and then concentrated under reduced pressure. After purification by silica gel column chromatography, elution being carried out with an ethyl acetate/cyclohexane mixture, 2.56 g of a white solid were obtained.

MH+: 204

6-chloro-4-(difluoromethyl)-3-iodo-1H-pyrazolo[3,4-b]pyridine 12.1 g (54.03 mmol) of N-iodosuccinimide were added, at ambient temperature under an inert nitrogen atmosphere, to 10 g (49.12 mmol) of 6-chloro-4-(difluoromethyl)-1H-pyrazolo[3,4-b]pyridine in 200 ml of dichloroethane. The reaction medium was heated at reflux for 9 hours and then hydrolyzed with a saturated aqueous sodium hydrogen carbonate solution. The aqueous phase was extracted with dichloromethane. The organic phase was washed with water, dried over sodium sulphate and then concentrated under reduced pressure. The solid obtained was taken up in a minimum amount of dichloromethane, filtered and then dried under reduced pressure at 50° C. for 18 hours.

12.63 g of a beige solid were obtained.

MH+: 330

Melting point: 175° C.

6-chloro-4-(difluoromethyl)-3-iodo-1-(tetrahydro-2H-pyran-2-yl)-1H-pyrazolo[3,4-b]pyridine 3.77 ml (41.34 mmol) of dihydropyran and 0.655 g (3.44 mmol) of PTSA were added, at 0° C., to 11.3 g (34.45 mmol) of 6-chloro-4-(difluoromethyl)-3-iodo-1H-pyrazolo[3,4-b]pyridine in 150 ml of anhydrous dichloromethane, under an inert nitrogen atmosphere. The reaction medium was stirred for 3 hours at ambient temperature and then hydrolyzed with water. The aqueous phase was extracted with dichloromethane. The organic phase obtained was washed with water, dried over sodium sulphate and then concentrated under reduced pressure. The residue obtained was taken up in a dichloromethane/pentane mixture. The precipitate obtained was filtered off, rinsed with pentane and then dried under reduced pressure at 50° C. for 18 hours. 11.93 g of a beige powder were obtained.

MH+=413

Melting point: 157° C.

6-chloro-4-(difluoromethyl)-3-phenyl-1-(tetrahydro-2H-pyran-2-yl)-1H-pyrazolo[3,4-b]pyridine 1.18 g (1.2 mmol) of phenylboronic acid, 14.40 g (58.03 mmol) of potassium phosphate dihydrate and 447 mg (0.39 mmol) of tetrakis(triphenylphosphine)palladium were added to 8 g (19.34 mmol) of 6-chloro-4-(difluoromethyl)-3-iodo-1-(tetrahydro-2H-pyran-2-yl)-1H-pyrazolo[3,4-b]pyridine in 4 ml of a DME/H$_2$O mixture (1/1) under an inert argon atmosphere. The reaction medium was heated at 90° C. under argon and then hydrolyzed with water and extracted with dichloromethane. The organic phase was dried over sodium sulphate and then concentrated under reduced pressure. The residue obtained was purified by silica gel column chromatography, elution being carried out with a heptane/dichloromethane mixture. 4.59 g of a white solid were obtained.

MH+=364

Melting point=122° C.

{4-[4-(difluoromethyl)-3-phenyl-1-(tetrahydro-2H-pyran-2-yl)-1H-pyrazolo[3,4-b]pyridin-6-yl]phenyl}(pyrrolidin-1-yl)methanone 0.263 g (1.2 mmol) of [4-(pyrrolidin-1-ylcarbonyl)phenyl]boronic acid, 0.747 g (3.01 mmol) of potassium phosphate dihydrate and 23 mg (0.02 mmol) of tetrakis(triphenylphosphine)palladium were added to 365 mg (1 mmol) of 6-chloro-4-(difluoromethyl)-3-phenyl-1-(tetrahydro-2H-pyran-2-yl)-1H-pyrazolo[3,4-b]pyridine in 4 ml of a DME/H$_2$O mixture (1/1) under an inert argon atmosphere. The reaction medium was microwave-heated at 150° C. for 15 minutes and then hydrolyzed with water and extracted with dichloromethane. The organic phase was dried over sodium sulphate and then concentrated under reduced pressure. The residue obtained was purified by silica gel column chromatography, elution being carried out with a dichloromethane/methanol mixture. 432 mg of a white foam were obtained.
MH+: 503
Melting point: 82° C.

{4-[4-(difluoromethyl)-3-phenyl-1H-pyrazolo[3,4-b]pyridin-6-yl]phenyl}(pyrrolidin-1-yl)methanone 1.07 ml of a 4 N solution of hydrochloric acid in dioxane were added, at ambient temperature under an inert nitrogen atmosphere, to 432 mg (0.86 mmol) of {4-[4-(difluoromethyl)-3-phenyl-1-(tetrahydro-2H-pyran-2-yl)-1H-pyrazolo[3,4-b]pyridin-6-yl]phenyl}(pyrrolidin-1-yl)methanone in 8 ml of methanol. The reaction medium was stirred for 4 hours at ambient temperature and then hydrolyzed with a saturated aqueous sodium hydrogen carbonate solution. The aqueous phase was extracted with dichloromethane, dried over sodium sulphate and then concentrated under reduced pressure. The white solid obtained was taken up in a dichloromethane/pentane mixture, filtered and then dried under reduced pressure at 50° C. for 18 hours. 300 mg of a white powder were obtained.
MH+: 419
Melting point: 248° C.
$^1$H NMR (400 MHz, DMSO-d$_6$) δ ppm: 14.27 (br. s, 1H) 8.29 (d, J=8.4 Hz, 2H) 8.03 (s, 1H) 7.71 (d, J=8.4 Hz, 2H) 7.65-7.69 (bs, 2H) 7.47-7.56 (bs, 3H) 7.33 (t, J=54.6 Hz, 1H) 3.51 (t, J=6.7 Hz, 2H) 3.45 (t, J=6.4 Hz, 2H) 1.78-1.96 (m, 4H)

EXAMPLE 3

Compound 8

2-amino-5-{3-phenyl-1-[2-(piperidin-1-yl)ethyl]-4-(trifluoromethyl)-1H-pyrazolo[3,4-b]pyridin-6-yl}benzonitrile 6-bromo-3-phenyl-1-[2-(piperidin-1-yl)ethyl]-4-(trifluoromethyl)-1H-pyrazolo[3,4-b]pyridine 0.403 g (2.19 mmol) of 1-(2-chloroethyl)piperidine hydrochloride and 0.606 g (4.38 mmol) of potassium carbonate were added, at ambient temperature, to 0.5 g (1.46 mmol) of 6-bromo-3-phenyl-4-(trifluoromethyl)-1H-pyrazolo[3,4-b]pyridine in 10 ml of anhydrous DMF, under an inert nitrogen atmosphere. The reaction medium was heated at 50° C. for 6 hours and then hydrolyzed with water. The aqueous phase was extracted with ethyl acetate. The organic phase obtained was washed with water, dried over sodium sulphate and then concentrated under reduced pressure. The orange oil obtained was purified by silica gel column chromatography, elution being carried out with a dichloromethane/methanol mixture. 0.440 g of a yellow oil were obtained.
MH+=454

2-amino-5-(4,4,5,5-tetramethyl-1,3,2-dioxaborolan-2-yl)benzonitrile 6 g (23.6 mmol) of 4,4,4',4',5,5,5',5'-octamethyl-2,2'-bis(1,3,2-dioxaborolane), 2.4 g (29.5 mmol) of sodium acetate, 540 mg (0.59 mmol) of tris(dibenzylideneacetone)dipalladium and 386 mg (1.38 mmol) of tricyclohexylphosphine were added to 3 g (19.7 mmol) of 2-amino-5-chlorobenzonitrile in 95 ml of dioxane under an inert argon atmosphere. The reaction medium was heated at 90° C. for 30 hours and then hydrolyzed with water and extracted with ethyl acetate. The organic phase was dried over sodium sulphate and then concentrated under reduced pressure. The residue obtained was taken up with petroleum ether. The precipitate obtained was filtered off and then dried under reduced pressure at 50° C. for 18 hours. 2.81 g of a white solid were obtained.
MH+: 245

2-amino-5-{3-phenyl-1-[2-(piperidin-1-yl)ethyl]-4-(trifluoromethyl)-1H-pyrazolo[3,4-b]pyridin-6-yl}benzonitrile 0.142 g (0.58 mmol) of 2-amino-5-(4,4,5,5-tetramethyl-1,3,2-dioxaborolan-2-yl)benzonitrile, 0.361 g (1.46 mmol) of potassium phosphate dihydrate and 11 mg (0.01 mmol) of tetrakis(triphenylphosphine)palladium were added to 220 mg (0.49 mmol) of 6-bromo-3-phenyl-1-[2-(piperidin-1-yl)ethyl]-4-(trifluoromethyl)-1H-pyrazolo[3,4-b]pyridine in 3 ml of a DME/H$_2$O mixture (1/1) under an inert argon atmosphere. The reaction medium was microwave-heated at 150° C. for 15 minutes and then hydrolyzed with water and extracted with dichloromethane. The organic phase was dried over sodium sulphate and then concentrated under reduced pressure. The residue obtained was purified by silica gel column chromatography, elution being carried out with a dichloromethane/methanol mixture. The beige solid obtained was taken up in a dichloromethane/pentane mixture, filtered and then dried under reduced pressure at 50° C. for 18 hours. 150 mg of a beige powder were obtained.
MH+: 491
Melting point: 195° C.
$^1$H NMR (400 MHz, DMSO-d$_6$) δ ppm: 8.49 (d, J=2.2 Hz, 1H) 8.34 (dd, J=8.9 Hz, 2.2 Hz, 1H) 8.10 (s, 1H) 7.49 (bs, 5H) 6.95 (d, J=8.9 Hz, 1H) 6.66 (s, 2H) 4.72 (t, J=6.5 Hz, 2H) 2.83 (t, J=6.5 Hz, 2H) 2.41-2.48 (bs, 4H) 1.28-1.41 (bs, 6H)

EXAMPLE 4

Compound 9

2-methoxy-5-[1-methyl-3-phenyl-4-(trifluoromethyl)-1H-pyrazolo[3,4-b]pyridin-6-yl]pyridine-3-carbonitrile 2-methoxy-5-[1-methyl-3-phenyl-4-(trifluoromethyl)-1H-pyrazolo[3,4-b]pyridin-6-yl]pyridine-3-carbonitrile 0.175 g (0.67 mmol) of 2-methoxy-5-(4,4,5,5-tetramethyl-1,3,2-dioxaborolan-2-yl)pyridine-3-carbonitrile, 0.418 g (1.68 mmol) of potassium phosphate dihydrate and 13 mg (0.01 mmol) of tetrakis(triphenylphosphine)palladium were added to 200 mg (0.56 mmol) of 6-bromo-1-methyl-3-phenyl-4-(trifluoromethyl)-1H-pyrazolo[3,4-b]pyridine in 3 ml of a DME/H$_2$O mixture (1/1) under an inert argon atmosphere. The reaction medium was microwave-heated at 150° C. for 15 minutes and then hydrolyzed with water and extracted with dichloromethane. The organic phase was dried over sodium sulphate and then concentrated under reduced pressure. The residue obtained was purified by silica gel column chromatography, elution being carried out with a heptane/dichloromethane mixture. The white solid obtained was taken up in a dichloromethane/pentane mixture, filtered and then dried under reduced pressure at 50° C. for 18 hours. 132 mg of a beige powder were obtained.

MH+: 410

Melting point: 250° C.

$^1$H NMR (400 MHz, DMSO-d$_6$) δ ppm 9.46 (d, J=2.5 Hz, 1H) 9.26 (d, J=2.5 Hz, 1H) 8.31 (s, 1H) 7.47-7.55 (bs, 5H) 4.27 (s, 3H) 4.12 (s, 3H)

EXAMPLE 5

Compound 8

2-amino-5-{4-(trifluoromethyl)-1-[2-(dimethylamino)ethyl]-1H-pyrazolo[3,4-b]pyridin-6-yl}benzonitrile 2-[6-bromo-3-phenyl-4-(trifluoromethyl)-1H-pyrazolo[3,4-b]pyridin-1-yl]-N,N-dimethylethanamine 0.252 g (1.75 mmol) of 2-chloro-N,N-dimethylethanamine hydrochloride and 0.484 g (3.51 mmol) of potassium carbonate were added, at ambient temperature, to 0.5 g (1.46 mmol) of 6-bromo-3-phenyl-4-(trifluoromethyl)-1H-pyrazolo[3,4-b]pyridine in 10 ml of anhydrous DMF, under an inert nitrogen atmosphere. The reaction medium was heated at 50° C. for 6 hours and then hydrolyzed with water. The aqueous phase was extracted with ethyl acetate. The organic phase obtained was washed with water, dried over sodium sulphate and then concentrated under reduced pressure. The orange oil obtained was purified by silica gel column chromatography, elution being carried out with a dichloromethane/methanol mixture. 0.271 g of a colourless oil was obtained.

MH+=414

2-amino-5-{4-(trifluoromethyl)-1-[2-(dimethylamino)ethyl]-1H-pyrazolo[3,4-b]pyridin-6-yl}benzonitrile 0.240 g (0.98 mmol) of 2-amino-5-(4,4,5,5-tetramethyl-1,3,2-dioxaborolan-2-yl)benzonitrile, 0.488 g (1.97 mmol) of potassium phosphate dihydrate and 15 mg (0.01 mmol) of tetrakis(triphenylphosphine)palladium were added to 271 mg (0.66 mmol) of 2-[6-bromo-3-phenyl-4-(trifluoromethyl)-1H-pyrazolo[3,4-b]pyridin-1-yl]-N,N-dimethylethanamine in 4 ml of a DME/H$_2$O mixture (1/1) under an inert argon atmosphere. The reaction medium was microwave-heated at 150° C. for 15 minutes and then hydrolyzed with water and extracted with dichloromethane. The organic phase was dried over sodium sulphate and then concentrated under reduced pressure. The residue obtained was purified by silica gel column chromatography, elution being carried out with a dichloromethane/methanol mixture. The solid obtained was taken up in a methanol/H$_2$O mixture, filtered and then dried under reduced pressure at 50° C. for 18 hours. 203 mg of a beige powder were obtained.

MH+: 451

Melting point: 183° C.

$^1$H NMR (400 MHz, DMSO-d$_6$) δ ppm: 8.49 (d, J=2.2 Hz, 1H) 8.34 (dd, J=9.0 Hz, 2.2 Hz, 1H) 8.11 (s, 1H) 7.46-7.52 (bs, 5H) 6.96 (d, J=9.0 Hz, 1H) 6.63-6.70 (bs, 2H) 4.71 (t, J=6.4 Hz, 2H) 2.85 (t, J=6.4 Hz, 2H) 2.21 (s, 6H)

EXAMPLE 6

Compound 11

2-amino-5-[4-(difluoromethyl)-3-(pyridin-3-yl)-1H-pyrazolo[3,4-b]pyridin-6-yl]benzonitrile 6-chloro-4-(difluoromethyl)-3-(pyridin-3-yl)-1-(tetrahydro-2H-pyran-2-yl)-1H-pyrazolo[3,4-b]pyridine 0.238 g (1.93 mmol) of pyridin-3-ylboronic acid, 1.44 g (5.80 mmol) of potassium phosphate dihydrate and 44 mg (0.04 mmol) of tetrakis(triphenylphosphine)palladium were added to 800 mg (1.93 mmol) of 6-chloro-4-(difluoromethyl)-3-iodo-1-(tetrahydro-2H-pyran-2-yl)-1H-pyrazolo[3,4-b]pyridine in 10 ml of a DME/H$_2$O mixture (1/1) under an inert argon atmosphere. The reaction medium was heated at 90° C. under argon and then hydrolyzed with water and extracted with dichloromethane. The organic phase was dried over sodium sulphate and then concentrated under reduced pressure. The residue obtained was purified by silica gel column chromatography, elution being carried out with a dichloromethane/methanol mixture. 517 mg of a yellow powder were obtained.

MH+: 365

2-amino-5-[4-(difluoromethyl)-3-(pyridin-3-yl)-1-(tetrahydro-2H-pyran-2-yl)-1H-pyrazolo[3,4-b]pyridin-6-yl]benzonitrile 0.160 g (0.67 mmol) of 2-amino-5-(4,4,5,5-tetramethyl-1,3,2-dioxaborolan-2-yl)benzonitrile, 0.408 g (1.64 mmol) of potassium phosphate dihydrate and 13 mg (0.01 mmol) of tetrakis(triphenylphosphine)palladium were added to 200 mg (0.55 mmol) of 6-chloro-4-(difluoromethyl)-3-(pyridin-3-yl)-1-(tetrahydro-2H-pyran-2-yl)-1H-pyrazolo[3,4-b]pyridine in 4 ml of a DME/H$_2$O mixture (1/1) under an inert argon atmosphere. The reaction medium was microwave-heated at 150° C. for 15 minutes and then hydrolyzed with water and extracted with dichloromethane. The organic phase was dried over sodium sulphate and then concentrated under reduced pressure. The residue obtained was purified by silica gel column chromatography, elution being carried out with a dichloromethane/methanol mixture. The yellow solid obtained was taken up in a dichloromethane/pentane mixture, filtered and then dried under reduced pressure at 50° C. for 18 hours. 204 mg of a yellow powder were obtained.

MH+: 447

Melting point: 150° C.

2-amino-5-[4-(difluoromethyl)-3-(pyridin-3-yl)-1H-pyrazolo[3,4-b]pyridin-6-yl]benzonitrile 0.57 ml of a 4 N solution of hydrochloric acid in dioxane was added, at ambient temperature under an inert nitrogen atmosphere, to 204 mg (0.46 mmol) of 2-amino-5-[4-(difluoromethyl)-3-(pyridin-3-yl)-1-(tetrahydro-2H-pyran-2-yl)-1H-pyrazolo[3,4-b]pyridin-6-yl]benzonitrile in 5 ml of an 8/2 dioxane/acetone mixture. The reaction medium was stirred for 24 hours and then methanol and 0.6 ml of a 4 N solution of hydrochloric acid in dioxane were added. The reaction medium was stirred for 24 hours and then hydrolyzed with a saturated aqueous sodium hydrogen carbonate solution. The precipitate obtained was filtered off, rinsed with water and then dried under reduced pressure at 50° C. for 18 hours. 131 mg of a yellow powder were obtained.

MH+: 363

Melting point: 296° C.

$^1$H NMR (400 MHz, DMSO-d$_6$): δ 14.26 (br. s., 1H) 8.82 (d, J=1.6 Hz, 1H) 8.68 (dd, J=4.8, 1.6 Hz, 1H) 8.33 (d, J=2.1 Hz, 1H) 8.24 (dd, J=8.9, 2.1 Hz, 1H) 8.05 (dt, J=7.9, 1.8 Hz, 1H) 7.98 (s, 1H) 7.54 (dd, J=7.9, 4.8 Hz, 1H) 7.28 (t, J=54.7 Hz, 1H) 6.95 (d, J=8.9 Hz, 1H) 6.62 (s, 2H)

EXAMPLE 7

Compound 12

2-amino-5-[4-(difluoromethyl)-3-(3-methoxyphenyl)-1H-pyrazolo[3,4-b]pyridin-6-yl]benzonitrile 6-chloro-4-(difluoromethyl)-3-(3-methoxyphenyl)-1-(tetrahydro-2H-pyran-2-yl)-1H-pyrazolo[3,4-b]pyridine 0.294 g (1.93 mmol) of pyridin-3-ylboronic acid, 1.44 g (5.80 mmol) of potassium phosphate dihydrate and 44 mg (0.04 mmol) of tetrakis(triphenylphosphine)palladium were added to 800 mg (1.93 mmol) of 6-chloro-4-(difluoromethyl)-3-iodo-1-(tetrahydro-2H-pyran-2-yl)-1H-pyrazolo[3,4-b]pyridine in 10 ml of a DME/H$_2$O mixture (1/1) under an inert argon atmosphere. The reaction medium was heated at 90° C. under an argon atmosphere and then hydrolyzed with water and extracted with dichloromethane. The organic phase was dried over sodium sulphate and then concentrated under reduced pressure. The residue obtained was purified by silica gel column chromatography, elution being carried out with a heptane/dichloromethane mixture. 655 mg of a white solid were obtained.

MH+: 394

Melting point: 144° C.

2-amino-5-[4-(difluoromethyl)-3-(3-methoxyphenyl)-1-(tetrahydro-2H-pyran-2-yl)-1H-pyrazolo[3,4-b]pyridin-6-yl]benzonitrile 0.149 g (0.61 mmol) of 2-amino-5-(4,4,5,5-tetramethyl-1,3,2-dioxaborolan-2-yl)benzonitrile, 0.478 g (1.52 mmol) of potassium phosphate dihydrate and 12 mg (0.01 mmol) of tetrakis(triphenylphosphine)palladium were added to 200 mg (0.51 mmol) of 6-chloro-4-(difluoromethyl)-3-(3-methoxyphenyl)-1-(tetrahydro-2H-pyran-2-yl)-1H-pyrazolo[3,4-b]pyridine in 3 ml of a DME/H$_2$O mixture (1/1) under an inert argon atmosphere. The reaction medium was microwave-heated at 150° C. for 15 minutes and then hydrolyzed with water and extracted with dichloromethane. The organic phase was dried over sodium sulphate and then concentrated under reduced pressure. The residue obtained was purified by silica gel column chromatography, elution being carried out with a heptane/dichloromethane mixture. The beige solid obtained was taken up in petroleum ether, filtered and then dried under reduced pressure at 50° C. for 18 hours. 204 mg of a yellow powder were obtained.

MH+: 476

Melting point: 130° C.

2-amino-5-[4-(difluoromethyl)-3-(3-methoxyphenyl)-1H-pyrazolo[3,4-b]pyridin-6-yl]benzonitrile 0.57 ml of a 4 N solution of hydrochloric acid in dioxane was added, at ambient temperature under an inert nitrogen atmosphere, to 165 mg (0.35 mmol) of 2-amino-5-[4-(difluoromethyl)-3-(3-methoxyphenyl)-1-(tetrahydro-2H-pyran-2-yl)-1H-pyrazolo[3,4-b]pyridin-6-yl]benzonitrile in 5 ml methanol. The reaction medium was stirred for 24 hours and then hydrolyzed with a saturated aqueous sodium hydrogen carbonate solution. The aqueous phase was extracted with dichloromethane. The organic phase was dried over sodium sulphate, filtered and then concentrated under reduced pressure. The residue obtained was taken up in petroleum ether. The precipitate obtained was filtered off, rinsed with water and then dried under reduced pressure at 50° C. for 18 hours. 86 mg of a yellow powder were obtained.

MH+: 392

Melting point: 233° C.

$^1$H NMR (400 MHz, DMSO-d$_6$) δ ppm 14.06 (br. s., 1H) 8.33 (d, J=1.6 Hz, 1H) 8.23 (dd, J=8.9 Hz, 1.6 Hz, 1H) 7.94 (s, 1H) 7.42 (t, J=8.0 Hz, 1H) 7.25 (t, J=54.6 Hz, 1H) 7.19-7.22 (bs, 2H) 7.05 (d, J=8.0 Hz, 1H) 6.94 (d, J=8.9 Hz, 1H) 6.60 (s, 2H) 3.82 (s, 3H)

EXAMPLE 8

Compound No. 14

N,N-dimethyl-4-[3-phenyl-4-(trifluoromethyl)-1H-pyrazolo[3,4-b]pyridin-6-yl]aniline 6-bromo-3-phenyl-4-(trifluoromethyl)-1-{[2-(trimethylsilyl)ethoxy]methyl}-1H-pyrazolo[3,4-b]pyridine 7.3 g (43.8 mmol) of [2-(chloromethoxy)ethyl(trimethyl)silane and 6.11 ml (43.8 mmol) of triethylamine are added, at ambient temperature, to 10 g (29 mmol) of 6-bromo-3-phenyl-4-(trifluoromethyl)-1H-pyrazolo[3,4-b]pyridine in 100 ml of anhydrous DMF, under an inert nitrogen atmosphere. The reaction medium is stirred for 2 hours and then hydrolyzed with water. The aqueous phase is extracted with ethyl acetate. The organic phase obtained is washed with water, dried over sodium sulphate and then concentrated under reduced pressure. The colourless oil obtained is purified by silica gel column chromatography, elution being carried out with a heptane/ethyl acetate mixture. 13.3 g of a colourless oil are obtained.

MH+=472

N,N-dimethyl-4-[3-phenyl-4-(trifluoromethyl)-1-{[2-(trimethylsilyl)ethoxy]methyl}-1H-pyrazolo[3,4-b]pyridin-6-yl]aniline 0.168 g (1.02 mmol) of [4-(dimethylamino)phenyl]boronic acid, 0.63 g (2.54 mmol) of potassium phosphate dihydrate and 19.6 mg (0.02 mmol) of tetrakis(triphenylphosphine)palladium are added to 0.4 g (0.85 mmol) of 6-bromo-3-phenyl-4-(trifluoromethyl)-1-{[2-(trimethylsilyl)ethoxy]methyl}-1H-pyrazolo[3,4-b]pyridine in 4 ml of a 1/1 DME/H$_2$O mixture under an inert argon atmosphere. The reaction medium is microwave-heated at 150° C. for 15 minutes. The reaction medium is hydrolyzed with water and then extracted with ethyl acetate. The organic phase is dried over sodium sulphate and then concentrated under reduced pressure. The residue obtained is purified by silica gel column chromatography, elution being carried out with a heptane/dichloromethane mixture. 380 mg of a yellow solid are obtained.

MH+: 513

Melting point: 98° C.

N,N-dimethyl-4-[3-phenyl-4-(trifluoromethyl)-1H-pyrazolo[3,4-b]pyridin-6-yl]aniline 3.56 ml (3.56 mmol) of a 1 N solution of TBAF in THF are added, at ambient temperature under an inert atmosphere, to 0.38 g (0.74 mmol) of N,N-dimethyl-4-[3-phenyl-4-(trifluoromethyl)-1-{[2-(trimethylsilyl)ethoxy]methyl}-1H-pyrazolo[3,4-b]pyridin-6-yl]aniline. The reaction medium is heated at reflux for 8 hours and then 1 ml of a 1 N solution of TBAF in THF is added and the heating is continued for eight hours. This step is repeated 3 times and then the reaction medium is hydrolyzed with water and concentrated under reduced pressure. The residue is taken up in an H$_2$O/methanol mixture. The precipitate obtained is filtered off, rinsed with water and dried at 50° C. under reduced pressure for 18 hours. 260 mg of a yellow solid are obtained.

MH+: 383

Melting point: 227° C.

$^1$H NMR (400 MHz, DMSO-d$_6$): δ 14.16 (br. s., 1H) 8.14 (d, J=9.1 Hz, 2H) 7.96 (s, 1H) 7.44-7.54 (bs, 5H) 6.85 (d, J=9.1 Hz, 2H) 3.03 (s, 6H)

EXAMPLE 9

Compound No. 19

2-amino-5-{4-(difluoromethyl)-1-[2-(dimethylamino)ethyl]-1H-pyrazolo[3,4-b]pyridin-6-yl}benzonitrile 6-chloro-4-(difluoromethyl)-3-iodo-1H-pyrazolo[3,4-b]pyridine 12.1 g (54.03 mmol) of N-iodosuccinimide are added, at ambient temperature under an inert nitrogen atmosphere, to 10 g (49.12 mmol) of 6-chloro-4-(difluoromethyl)-1H-pyrazolo[3,4-b]pyridine in 200 ml of dichloroethane. The reaction medium is heated at reflux for 9 hours and then hydrolyzed with a saturated aqueous sodium hydrogen carbonate solution. The reaction medium is extracted with dichloromethane. The organic phase is washed with water, dried over sodium sulphate and then concentrated under reduced pressure. The solid obtained is taken up in a minimum amount of dichloromethane, filtered and then dried under reduced pressure at 50° C. for 18 hours. 12.63 g of a beige solid are obtained.

MH+: 330

Melting point: 175° C.

2-[6-chloro-4-(difluoromethyl)-3-iodo-1H-pyrazolo[3,4-b]pyridin-1-yl]-N,N-dimethylethanamine 1 g (7.28 mmol) of 2-chloro-N,N-dimethylethanamine hydrochloride and 4.74 g (14.57 mmol) of caesium carbonate are added, at ambient temperature, to 2 g (6.07 mmol) of 6-chloro-4-(difluoromethyl)-3-iodo-1H-pyrazolo[3,4-b]pyridine in 30 ml of anhydrous DMF, under an inert nitrogen atmosphere. The reaction medium is stirred for 6 hours and then 0.5 g of 2-chloro-N,N-dimethylethanamine hydrochloride and 2.4 g of caesium carbonate are added. The reaction medium is stirred for 18 hours at ambient temperature and then hydrolyzed with water. The aqueous phase is extracted with ethyl acetate. The organic phase obtained is washed with water, dried over sodium sulphate and then concentrated under reduced pressure. The brown oil obtained is purified by silica gel column chromatography, elution being carried out with a dichloromethane/methanol mixture. 1.51 g of a beige solid are obtained.

MH+=401

2-[6-chloro-4-(difluoromethyl)-3-phenyl-1H-pyrazolo[3,4-b]pyridin-1-yl]-N,N-dimethylethanamine 0.06 g (0.5 mmol) of phenylboronic acid, 0.371 g (1.5 mmol) of potassium phosphate dihydrate and 11 mg (0.01 mmol) of tetrakis(triphenylphosphine)palladium are added to 200 mg (0.5 mmol) of 2-[6-chloro-4-(difluoromethyl)-3-iodo-1H-pyrazolo[3,4-b]pyridin-1-yl]-N,N-dimethylethanamine in 3 ml of a 1/1 DME/H$_2$O mixture under an inert argon atmosphere. The reaction medium is heated at 90° C. in a sealed tube for 24 hours. The reaction medium is hydrolyzed with water and then extracted with dichloromethane. The organic phase is dried over sodium sulphate and then concentrated under reduced pressure. The residue obtained is purified by silica gel column chromatography, elution being carried out with a dichloromethane/methanol mixture. 0.07 g of a yellow oil is obtained.

MH+: 351

2-amino-5-{4-(difluoromethyl)-1-[2-(dimethylamino)ethyl]-1H-pyrazolo[3,4-b]pyridin-6-yl}benzonitrile 0.178 g (0.73 mmol) of 2-amino-5-(4,4,5,5-tetramethyl-1,3,2-dioxaborolan-2-yl)benzonitrile, 0.452 g (1.82 mmol) of potassium phosphate dihydrate and 14 mg (0.01 mmol) of tetrakis(triphenylphosphine)palladium are added to 213 mg (0.61 mmol) of 2-[6-chloro-4-(difluoromethyl)-3-phenyl-1H-pyrazolo[3,4-b]pyridin-1-yl]-N,N-dimethylethanamine in 3 ml of a 1/1 DME/H$_2$O mixture under an inert argon atmosphere. The reaction medium is microwave-heated at 150° C. for 15 minutes. The reaction medium is hydrolyzed with water and then extracted with dichloromethane. The organic phase is dried over sodium sulphate and then concentrated under reduced pressure. The residue obtained is purified by silica gel column chromatography, elution being carried out with a dichloromethane/methanol mixture. The residue obtained is taken up in a dichloromethane/pentane mixture. The precipitate obtained is filtered off and then dried under reduced pressure at 50° C. for 18 hours. 0.161 g of a white solid is obtained.

MH+: 433

Melting point: 163° C.

$^1$H NMR (400 MHz, DMSO-d$_6$) δ 8.40 (d, J=2.2 Hz, 1H), 8.30 (dd, J=9.0, 2.2 Hz, 1H), 7.96 (s, 1H), 7.65 (dd, J=7.7, 1.7 Hz, 2H), 7.46-7.55 (bs, 3H), 7.28 (t, J=54.6 Hz, 1H), 6.96 (d, J=9.0 Hz, 1H), 6.62 (s, 2H), 4.69 (t, J=6.3 Hz, 2H), 2.85 (t, J=6.3 Hz, 2H), 2.21 (s, 6H)

TABLE
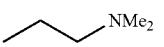
| No. | R₂ | R₃ | R₁ | R₄ | Salt | m.p. (° C.) | M + H⁺ |
|---|---|---|---|---|---|---|---|
| 1 | CF₃ | Ph | 3-CONH₂-phenyl | Me | / | / | 397 |
| 2 | CF₃ | Ph | 2-F-5-CONHMe-phenyl | Me | / | / | 429 |
| 3 Ex 1 | CF₃ | Ph | 3-NMe₂-phenyl | Me | / | / | 397 |
| 4 | CF₃ | Ph | 3-CONMe₂-phenyl | Me | / | / | 425 |
| 5 Ex 2 | CHF₂ | Ph | 4-(pyrrolidin-1-ylcarbonyl)phenyl | H | HCl | 248 | 455 |
| 6 | CHF₂ | Ph | 3-(pyrrolidin-1-ylcarbonyl)phenyl | H | HCl | / | 455 |
| 7 | CHF₂ | Ph | 3-(piperidin-1-yl)phenyl | H | HCl | / | 441 |
| 8 Ex 5 | CF₃ | Ph | 2-NH₂-3-CN-phenyl | CH₂CH₂CH₂NMe₂ | / | 183 | 451 |

TABLE-continued (I')

| No. | R$_2$ | R$_3$ | R$_1$ | R$_4$ | Salt | m.p. (° C.) | M + H$^+$ |
|---|---|---|---|---|---|---|---|
| 9 Ex 4 | CF$_3$ | Ph | 5-methyl-2-methoxy-3-cyanopyridin-yl | Me | / | 250 | 410 |
| 10 Ex 3 | CF$_3$ | Ph | 2-amino-3-cyanophenyl | propyl-piperidinyl | / | 192 | 491 |
| 11 Ex 6 | CHF$_2$ | 3-py | 2-amino-3-cyanophenyl | H | / | 296 | 363 |
| 12 Ex 7 | CHF$_2$ | 3MeO—Ph | 2-amino-3-cyanophenyl | Me | / | 233 | 392 |
| 13 | CF$_3$ | Ph | 3-NHSO$_2$Me-phenyl | H | HCl | / | 433 |
| 14 Ex 8 | CHF$_2$ | Ph | 2-amino-3-cyanophenyl | propyl-NMe$_2$ | / | 163 | 433 |
| 15 | CF$_3$ | Ph | benzimidazol-2-one-yl | H | / | 380 | 396 |
| 16 | CF$_3$ | Ph | 4-aminophenyl | H | / | 237 | 355 |
| 17 | CF$_3$ | Ph | 3-CONHMe-phenyl | H | HCl | / | 397 |
| 18 | CF$_3$ | Ph | 4-OMe-phenyl | Me | / | 181 | 384 |

TABLE-continued (I')

| No. | R₂ | R₃ | R₁ | R₄ | Salt | m.p. (° C.) | M + H⁺ |
|---|---|---|---|---|---|---|---|
| 19 Ex 9 | CF₃ | Ph | 4-NMe₂-phenyl | H | / | 227 | 383 |
| 20 | CF₃ | Ph | 4-F,3-CN-phenyl | H | / | / | 383 |
| 21 | CF₃ | Ph | 3-NHSO₂Me-phenyl | Me | / | / | 447 |
| 22 | CHF₂ | Ph | 4-NH₂,3-CN-phenyl | H | HCl | 282 | 362 |
| 23 | CF₃ | Ph | 4-COOH-phenyl | Me | / | / | 398 |
| 24 | CF₃ | Ph | 4-morpholino-phenyl | H | HCl | / | 425 |

The compounds according to the invention were subjected to pharmacological tests for determining their activity for the treatment of bladder cancer.

EXAMPLE 10

Evaluation of the Capacity of the FGF-R Antagonists to Inhibit Serum-Induced Proliferation of Bladder Cancer Tumour Cells of TCC97-7 Type Carrying the Ser249Cys Mutation of FGF Receptor 3

To do this, 2000 cells are seeded in the morning in 50 μl of complete medium (Ham-F/12, 1% FCS, 2 mM glutamine, non-essential amino acids, sodium pyruvate, 1% insulin/transferrin/selenium, hydrocortisone). In the evening, 50 μl of the various compounds are added at 2 or 20 μM after dilution in complete culture medium in order to obtain final concentrations of 1 or 10 μM. After 3 days, cell proliferation is evaluated by measuring the cell-covered surface area of a well of a 96 well plate. This surface area is measured using an Incucyte apparatus (Essen BioScience). The percentage inhibition of the cell proliferation is calculated by considering the surface area occupied by the TCC97-7 cells cultured in the absence of FGF-R antagonists to be 0% inhibition. 100% inhibition would correspond to a well no longer containing cells. The compounds of the present invention are considered to be active from the moment an inhibition of greater than or equal to 20% at the dose of less than or equal to 10 μM is observed.

Thus, compounds 1 to 24 are capable of inhibiting TCC97-7 cell proliferation by more than 20% at the dose of 1 or 10 μM. (Table No. 2).

TABLE NO. 2

Evaluation of the compounds with regard to their capacity to inhibit the proliferation of the TCC97-7 cell line in the presence of serum

| | Inhibition of proliferation (%) | |
|---|---|---|
| | 1 μM | 10 μM |
| compound 1 | 8.0 | 91.6 |
| compound 2 | 4.0 | 53.2 |
| compound 3 | −32.3 | 40.0 |
| compound 4 | 5.0 | 64.4 |

TABLE NO. 2-continued

Evaluation of the compounds with regard to their capacity to inhibit the proliferation of the TCC97-7 cell line in the presence of serum

| | Inhibition of proliferation (%) | |
|---|---|---|
| | 1 μM | 10 μM |
| compound 5 | 45.7 | 19.5 |
| compound 6 | 16.2 | 83.9 |
| compound 7 | −50.3 | 52.2 |
| compound 8 | 10.8 | 95.2 |
| compound 9 | 27.6 | 79.7 |
| compound 10 | 22.8 | 85.9 |
| compound 11 | 50.4 | 19.2 |
| compound 12 | 12.1 | 95.8 |
| compound 13 | 0 | 57 |
| compound 15 | −3 | 29 |
| compound 21 | −3 | 61 |
| compound 23 | 8 | 33 |

EXAMPLE 11

Evaluation of the Capacity of FGF-R Antagonists to Reduce the ATP Content of TCC97-7 Bladder Cancer Cells Carrying the Ser249Cys Mutation of FGF-R3, Cultured in a Serum-Supplemented Medium To do this, 3000 cells are seeded in 50 μl of complete medium (Ham-F/12, 1% FCS, 2 mM glutamine, non-essential amino acids, sodium pyruvate, 1% insulin/transferrin/selenium, hydrocortisone). 16 hours later, 50 μl of the various compounds are added at 2 and 20 μM after dilution in complete culture medium in order to obtain final concentrations of 1 and 10 μM. After 3 days, the ATP content of the cells is measured using the Cell Titer-Glo® Luminescent Cell Viability Assay kit (Promega, France) according to the supplier's recommendations. The percentage inhibition of the amount of intracellular ATP is calculated by considering the ATP content of the cells cultured in the absence of antagonist to be 0% inhibition. 100% inhibition would correspond to a well in which the ATP content is zero. The compounds of the present invention are considered to be active from the moment an inhibition of greater than or equal to 20% at the dose of less than or equal to 10 μM is observed.

Thus, compounds 1 to 24 are capable of inhibiting the amount of intracellular ATP in TCC97-7 cells by more than 20% at the dose of 1 or 10 μM (Table No. 3).

TABLE NO. 3 measurement of the inhibition of the amount of intracellular ATP in TCC97-7 cells cultured in the presence of serum and brought into contact with various compounds

| | Inhibition of the amount of intracellular ATP (%) | |
|---|---|---|
| | 1 μM | 10 μM |
| compound 1 | 10.9 | 41.1 |
| compound 2 | 17.9 | 35.9 |
| compound 3 | 21.3 | 47.7 |
| compound 4 | 23.7 | 49.6 |
| compound 5 | 37.1 | 40.8 |
| compound 6 | 26.9 | 90.5 |
| compound 7 | 20.4 | 78.0 |
| compound 8 | 27.7 | 97.8 |
| compound 9 | 12.3 | 69.3 |
| compound 10 | 11.0 | 94.4 |
| compound 11 | 21.5 | 25.5 |
| compound 12 | 23.8 | 75.8 |
| compound 13 | 56 | 63 |
| compound 14 | 32 | 77 |
| compound 15 | −11 | 19 |
| compound 16 | 24 | 38 |
| compound 17 | 13 | 69 |
| compound 18 | 16 | 44 |
| compound 19 | 30 | 63 |
| compound 20 | 11 | 26 |
| compound 21 | −1 | 25 |
| compound 22 | 27 | 53 |
| compound 23 | 17 | 40 |
| compound 24 | 6 | 27 |

According to another of its aspects, the present invention relates to the use of pharmaceutical compositions comprising, as active ingredient, a compound of formula (I) for the treatment of bladder cancer. These pharmaceutical compositions contain an effective dose of at least one compound according to formula (I), or a pharmaceutically acceptable salt, and also at least one pharmaceutically acceptable excipient, used for the treatment of bladder cancer. Said excipients are chosen, according to the pharmaceutical form and the mode of administration desired, from the usual excipients which are known to those skilled in the art.

According to another of its aspects, the present invention relates to the use of a compound as above described for preparing a medicament for the treatment of bladder cancers, and particularly under their superficial forms, expressing the wild type or mutant FGFR3 gene.

According to another of its aspects, the present invention relates to the use of a compound as above described for preparing a medicament for the treatment of bladder cancers, and particularly under their superficial forms expressing the wild type form of the gene TP53.

According to another of its aspects, the present invention relates to the use of a compound as above described for preparing a medicament for the treatment of bladder cancers where the bladder cancers are non muscle-invasive.

In the pharmaceutical compositions for oral, sublingual, subcutaneous, intramuscular, intravenous, topical, local, intratracheal, intranasal, transdermal, intravesical or rectal administration, the active ingredient of formula (I) above, or its optional salt, solvate or hydrate, can be administered in unit administration form, as a mixture with conventional pharmaceutical excipients, to animals and to human beings for the prophylaxis or treatment of the abovementioned disorders or diseases.

The appropriate unit administration forms include oral forms, such as tablets, soft or hard gel capsules, powders, granules and oral solutions or suspensions, sublingual, buccal, intratracheal, intraocular and intranasal administration forms, forms of administration by inhalation, topical, transdermal, subcutaneous, intramuscular, intravesical or intravenous administration forms, rectal administration forms, and implants. For topical application, the compounds according to formula (I) can be used in creams, gels, ointments or lotions.

The pharmaceutical compositions according to the use of the present invention are preferably administered orally.

By way of example, a unit administration form of a compound according to the invention in tablet form may comprise the following constituents:

| | |
|---|---|
| FGF receptor inhibitor compound | 50.0 mg |
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

The present invention also relates to a pharmaceutical composition as defined above, as a medicament for the treatment of bladder cancer.

A compound of formula (I) according to the use of the present invention can be administered alone or in combination with one or more compound(s) having an anti-angiogenic activity or with one or more cytotoxic compound(s) (chemotherapy), or else in combination with a radiation treatment. Thus, a subject of the present invention is also the use of a compound of formula (I), as defined above, in combination with one or more anti-cancer active ingredient(s) and/or with radiotherapy.

The compositions according to the invention, for oral administration, contain recommended doses of from 0.01 to 700 mg. There may be particular cases where higher or lower dosages are appropriate; such dosages do not depart from the context of the invention. According to the usual practice, the dosage appropriate for each patient is determined by the physician according to the mode of administration and the age, weight and response of the patient, and also according to the degree of progression of the disease.

According to another of its aspects, the present invention also relates to a method for treating bladder cancer, which comprises the administration, to a patient, of an effective dose of a compound according to the invention, or a pharmaceutically acceptable salt thereof.

The invention claimed is:

1. A method for treating a bladder cancer comprising administering to a patient in need thereof a pharmaceutically effective amount of a compound of formula (I):

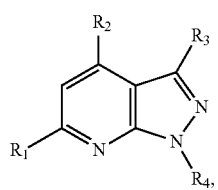

(I)

or a pharmaceutically acceptable salt thereof, wherein:
$R_1$ is an aryl or heteroaryl group optionally substituted with one or more substituents independently selected from the group consisting of:
  a halogen atom,
  a cyano group,
  an —$NR_5R_5'$ group, where $R_5$ and $R_5'$ are independently a hydrogen atom or a linear alkyl group,
  an —$NR_7R_8$ group, where $R_7$ and $R_8$ form, together with the nitrogen atom to which they are attached, a heterocycloalkyl comprising one or more heteroatoms independently selected from the group consisting of a nitrogen atom and an oxygen atom,
  a —$COR_{10}$ group, where $R_{10}$ is a hydroxyl group or an —$NR_5R_5'$ group, where $R_5$ and $R_5'$ are independently a hydrogen atom or a linear alkyl group,
  a —$CONR_6R_6'$ group, where $R_6$ and $R_6'$ form, together with the nitrogen atom to which they are attached, a heterocycloalkyl comprising one or more heteroatoms independently selected from the group consisting of a nitrogen atom and an oxygen atom,
  an —$NHSO_2CH_3$ group, and
  an —$OR_9$ group, where $R_9$ is a linear ($C_1$-$C_3$)alkyl group; or $R_1$ is a bicyclic group of formula A:

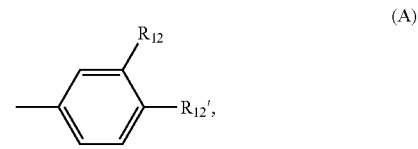

(A)

wherein $R_{12}$ and $R_{12}'$ form, together with the carbon atoms to which they are attached, a heterocycloalkyl comprising one or more heteroatoms independently selected from the group consisting of a nitrogen atom and an oxygen atom;
$R_2$ is a haloalkyl group;
$R_3$ is:
  an aryl group, optionally substituted with one or more alkoxy groups, or
  a heteroaryl group; and
$R_4$ is:
  a hydrogen atom, or
  a linear ($C_1$-$C_3$)alkyl group, optionally substituted with an —$NR_5R_5'$ group, where $R_5$ and $R_5'$ are independently a hydrogen atom or a linear alkyl group, or an —$NR_6R_6'$ group, where $R_6$ and $R_6'$ form, together with the nitrogen atom to which they are attached, a heterocycloalkyl comprising one or more heteroatoms independently selected from the group consisting of a nitrogen atom and an oxygen atom;
provided that the compound of formula (I) is other than 3-(3-methoxyphenyl)-6-(4-methoxyphenyl)-1-methyl-4-(trifluoromethyl)pyrazolo[3,4-b]pyridine.

2. The method of claim 1, wherein
$R_1$ is an aryl or heteroaryl group optionally substituted with one or more substituents independently selected from the group consisting of:
  a halogen atom,
  a cyano group,
  an —$NR_5R_5'$ group where $R_5$ and $R_5'$ are independently a hydrogen atom or a linear alkyl group,
  an —$NR_7R_8$ group, where $R_7$ and $R_8$ form, together with the nitrogen atom to which they are attached, a heterocycloalkyl comprising one or more heteroatoms independently selected from the group consisting of a nitrogen atom and an oxygen atom,
  a —$CONR_5R_5'$ group, where $R_5$ and $R_5'$ are independently a hydrogen atom or a linear alkyl group,
  a —$CONR_6R_6'$ group, where $R_6$ and $R_6'$ form, together with the nitrogen atom to which they are attached, a heterocycloalkyl comprising one or more heteroatoms independently selected from the group consisting of a nitrogen atom and an oxygen atom, and an —OR$_9$ group where R$_9$ is a linear (C$_1$-C$_3$)alkyl group.

3. The method of claim 1, wherein R$_2$ is a haloalkyl group selected from the group consisting of a —CF$_3$ group and a —CHF$_2$ group.

4. The method of claim 2, wherein R$_2$ is a haloalkyl group selected from the group consisting of a —CF$_3$ group and a —CHF$_2$ group.

5. The method of claim 3, wherein

R$_1$ is a phenyl or pyridinyl group optionally substituted with one or more substituents independently selected from the group consisting of:
a fluorine atom,
a cyano group,
an —NR$_5$R$_5$' group where R$_5$ and R$_5$' are independently a hydrogen atom or a linear alkyl group,
an —NR$_7$R$_8$ group, where R$_7$ and R$_8$ form, together with the nitrogen atom to which they are attached, a heterocycloalkyl comprising one or more heteroatoms independently selected from the group consisting of a nitrogen atom and an oxygen atom,
a —COR$_{10}$ group where R$_{10}$ is a hydroxyl group or an —NR$_5$R$_5$' group where R$_5$ and R$_5$' are independently a hydrogen atom or a linear alkyl group,
a —CONR$_6$R$_6$' group where R$_6$ and R$_6$' form, together with the nitrogen atom to which they are attached, a heterocycloalkyl comprising one or more heteroatoms independently selected from the group consisting of a nitrogen atom and an oxygen atom,
an —NHSO$_2$CH$_3$ group, and
an —OR$_9$ group where R$_9$ is a linear (C$_1$-C$_3$)alkyl group;
or R$_1$ is a bicyclic group of formula A:

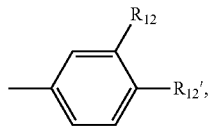

(A)

wherein R$_{12}$ and R$_{12}$' form, together with the carbon atoms to which they are attached, a heterocycloalkyl comprising one or more heteroatoms independently selected from the group consisting of a nitrogen atom and an oxygen atom.

6. The method of claim 4, wherein:

R$_1$ is a phenyl or pyridinyl group optionally substituted with one or more substituents independently selected from the group consisting of:
a fluorine atom,
a cyano group,
an —NR$_5$R$_5$' group where R$_5$ and R$_5$' are independently a hydrogen atom or a linear (C$_1$-C$_3$)alkyl group,
an —NR$_7$R$_8$ group, where R$_7$ and R$_8$ form, together with the nitrogen atom to which they are attached, a heterocycloalkyl comprising one or more heteroatoms independently selected from the group consisting of a nitrogen atom and an oxygen atom,
a —CONR$_5$R$_5$' group, where R$_5$ and R$_5$' are independently a hydrogen atom or a linear (C$_1$-C$_3$)alkyl group,
a —CONR$_6$R$_6$' group where R$_6$ and R$_6$' form, together with the nitrogen atom to which they are attached, a heterocycloalkyl comprising one or more heteroatoms independently selected from the group consisting of a nitrogen atom and an oxygen atom, and
an —OR$_9$ group where R$_9$ is a methyl group;

R$_3$ is:
an aryl group, optionally substituted with a methoxy group, or
a pyridinyl group; and R$_4$ is:
a hydrogen atom, or
a linear (C$_1$-C$_2$)alkyl group, optionally substituted with an —NR$_5$R$_5$' group where R$_5$ and R$_5$' are independently a hydrogen atom or a linear (C$_1$-C$_3$)alkyl group, or an —NR$_6$R$_6$' group, where R$_6$ and R$_6$' form, together with the nitrogen atom to which they are attached, a heterocycloalkyl comprising one or more heteroatoms independently selected from the group consisting of a nitrogen atom and an oxygen atom.

7. The method of claim 1, wherein:

R$_1$ is a phenyl group optionally substituted with one or more substituents independently selected from the group consisting of:
a halogen atom,
a cyano group,
an —NR$_5$R$_5$' group where R$_5$ and R$_5$' are independently a hydrogen atom or a linear (C$_1$-C$_3$)alkyl group,
an —NR$_7$R$_8$ group, where R$_7$ and R$_8$ form, together with the nitrogen atom to which they are attached, a heterocycloalkyl comprising one or more heteroatoms independently selected from the group consisting of a nitrogen atom and an oxygen atom,
a —COR$_{10}$ group where R$_{10}$ is a hydroxyl group or an —NR$_5$R$_5$' group where R$_5$ and R$_5$' are independently a hydrogen atom or a linear (C$_1$-C$_3$)alkyl group,
a —CONR$_6$R$_6$' group where R$_6$ and R$_6$' form, together with the nitrogen atom to which they are attached, a heterocycloalkyl comprising one or more heteroatoms independently selected from the group consisting of a nitrogen atom and an oxygen atom,
an —NHSO$_2$CH$_3$ group, and
an —OR$_9$ group where R$_9$ is a linear (C$_1$-C$_3$)alkyl group;
or R$_1$ represents a bicyclic group of formula A:

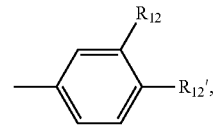

(A)

wherein R$_{12}$ and R$_{12}$' form, together with the carbon atoms to which they are attached, a heterocycloalkyl comprising one or more heteroatoms independently selected from the group consisting of a nitrogen atom and an oxygen atom;

R$_3$ is:
an aryl group, optionally substituted with a methoxy group, or
a pyridinyl group; and R$_4$ is:
a hydrogen atom, or
a linear (C$_1$-C$_2$)alkyl group, optionally substituted with an —NR$_5$R$_5$' group where R$_5$ and R$_5$' are independently a hydrogen atom or a linear (C$_1$-C$_3$)alkyl group, or an —NR$_6$R$_6$' group, where R$_6$ and R$_6$' form, together with the nitrogen atom to which they are attached, a heterocycloalkyl.

8. The method of claim 2, wherein:
$R_1$ is a phenyl group optionally substituted with one or more substituents independently selected from the group consisting of:
- a halogen atom,
- a cyano group,
- an —$NR_5R_5'$ group where $R_5$ and $R_5'$ are independently a hydrogen atom or a linear ($C_1$-$C_3$)alkyl group,
- an —$NR_7R_8$ group, where $R_7$ and $R_8$ form, together with the nitrogen atom to which they are attached, a heterocycloalkyl comprising one or more heteroatoms independently selected from the group consisting of a nitrogen atom and an oxygen atom,
- a —$CONR_5R_5'$ group, where $R_5$ and $R_5'$ are independently a hydrogen atom or a linear ($C_1$-$C_3$)alkyl group,
- a —$CONR_6R_6'$ group where $R_6$ and $R_6'$ form, together with the nitrogen atom to which they are attached, a heterocycloalkyl comprising one or more heteroatoms independently selected from the group consisting of a nitrogen atom and an oxygen atom, and
- an —$OR_9$ group where $R_9$ is a linear ($C_1$-$C_3$)alkyl group;

$R_3$ is:
- an aryl group, optionally substituted with a methoxy group, or
- a pyridinyl group; and $R_4$ is:
- a hydrogen atom, or
- a linear ($C_1$-$C_2$)alkyl group, optionally substituted with an —$NR_5R_5'$ group where $R_5$ and $R_5'$ are independently a hydrogen atom or a linear ($C_1$-$C_3$)alkyl group, or an
  —$NR_6R_6'$ group such that where $R_6$ and $R_6'$ form, together with the nitrogen atom to which they are attached, a heterocycloalkyl comprising one or more heteroatoms independently selected from the group consisting of a nitrogen atom and an oxygen atom.

9. The method of claim 1, wherein
$R_1$ is a pyridinyl group optionally substituted with one or more substituents independently selected from the group consisting of:
- a cyano group, and
- an —$OR_9$ group, where $R_9$ represents a linear ($C_1$-$C_3$) alkyl group.

10. The method of claim 1, wherein $R_4$ is a hydrogen atom.

11. The method of claim 1, wherein $R_4$ is
a linear ($C_1$-$C_3$)alkyl group, optionally substituted with an —$NR_5R_5'$ group, where $R_5$ and $R_5'$ are independently a hydrogen atom or a linear alkyl group, or an —$NR_6R_6'$ group such that where $R_6$ and $R_6'$ form, together with the nitrogen atom to which they are attached, a heterocycloalkyl comprising one or more heteroatoms independently selected from the group consisting of a nitrogen atom and an oxygen atom.

12. The method of claim 1, wherein the compound is selected from the group consisting of:
3-(1-methyl-3-phenyl-4-trifluoromethyl-1H-pyrazolo[3,4-b]pyridin-6-yl)benzamide,
2-Fluoro-N-methyl-5-(1-methyl-3-phenyl-4-trifluoromethyl-1H-pyrazolo[3,4-b]pyridin-6-yl)benzamide,
Dimethyl-[3-(1-methyl-3-phenyl-4-trifluoromethyl-1H-pyrazolo[3,4-b]pyridin-6-yl)phenyl]amine,
N,N-Dimethyl-3-(1-methyl-3-phenyl-4-trifluoromethyl-1H-pyrazolo[3,4-b]pyridin-6-yl)benzamide,
[4-(4-Difluoromethyl-3-phenyl-1H-pyrazolo[3,4-b]pyridin-6-yl)-phenyl]pyrrolidin-1-ylmethanone,
[3-(4-Difluoromethyl-3-phenyl-1H-pyrazolo[3,4-b]pyridin-6-yl)phenyl]pyrrolidin-1-ylmethanone,
4-Difluoromethyl-3-phenyl-6-(3-piperidin-1-ylphenyl)-1H-pyrazolo[3,4-b]pyridine,
2-Amino-5-[1-(2-dimethylamino-ethyl)-3-phenyl-4-trifluoromethyl-1H-pyrazolo[3,4-b]pyridin-6-yl]benzonitrile,
2-Methoxy-5-(1-methyl-3-phenyl-4-trifluoromethyl-1H-pyrazolo[3,4-b]pyridin-6-yl)nicotinonitrile,
2-Amino-5-[3-phenyl-1-(2-piperidin-1-ylethyl)-4-trifluoromethyl-1H-pyrazolo[3,4-b]pyridin-6-yl]benzonitrile,
2-Amino-5-(4-difluoromethyl-3-pyridin-3-yl-1H-pyrazolo[3,4-b]pyridin-6-yl)benzonitrile,
2-Amino-5-[4-difluoromethyl-3-(3-methoxyphenyl)-1H-pyrazolo[3,4-b]pyridin-6-yl]benzonitrile,
N-[3-(3-Phenyl-4-trifluoromethyl-1H-pyrazolo[3,4-b]pyridin-6-yl)phenyl]methanesulphonamide hydrochloride,
2-Amino-5-[4-difluoromethyl-1-(2-dimethylaminoethyl)-3-phenyl-1H-pyrazolo[3,4-b]pyridin-6-yl]benzonitrile,
5-(3-Phenyl-4-trifluoromethyl-1H-pyrazolo[3,4-b]pyridin-6-yl)-1,3-dihydrobenzoimidazol-2-one,
4-(3-Phenyl-4-trifluoromethyl-1H-pyrazolo[3,4-b]pyridin-6-yl)phenylamine,
N-Methyl-3-(3-phenyl-4-trifluoromethyl-1H-pyrazolo[3,4-b]pyridin-6-yl)benzamide hydrochloride,
6-(4-Methoxyphenyl)-3-phenyl-4-trifluoromethyl-1H-pyrazolo[3,4-b]pyridine,
Dimethyl-[4-(3-phenyl-4-trifluoromethyl-1H-pyrazolo[3,4-b]pyridin-6-yl)phenyl]amine,
2-Fluoro-5-(3-phenyl-4-trifluoromethyl-1H-pyrazolo[3,4-b]pyridin-6-yl)benzonitrile,
N-[3-(1 Methyl-3-phenyl-4-trifluoromethyl-1H-pyrazolo[3,4-b]pyridin-6-yl)phenyl]methanesulphonamide,
2-Amino-5-(4-difluoromethyl-3-phenyl-1H-pyrazolo[3,4-b]pyridin-6-yl)benzonitrile hydrochloride,
4-(1-Methyl-3-phenyl-4-trifluoromethyl-1H-pyrazolo[3,4-b]pyridin-6-yl)benzoic acid, and
6-(4-Morpholin-4-ylphenyl)-3-phenyl-4-trifluoromethyl-1H-pyrazolo[3,4-b]pyridine hydrochloride;
or a pharmaceutically acceptable salt thereof.

13. The method of claim 1, wherein the bladder cancer under its superficial form expresses the wild type or mutant FGFR3 gene.

14. The method of claim 1, wherein the bladder cancer under its superficial form expresses the wild type form of the gene TP53.

15. The method of claim 1, wherein the bladder cancer is a non muscle-invasive bladder cancer.

16. The method of claim 7, wherein $R_2$ is a haloalkyl group selected from the group consisting of a —$CF_3$ group and a —$CHF_2$ group.

17. The method of claim 8, wherein $R_2$ is a haloalkyl group selected from the group consisting of a —$CF_3$ group and a —$CHF_2$ group.

18. The method of claim 12, wherein the bladder cancer under its superficial form expresses the wild type or mutant FGFR3 gene.

19. The method of claim 12, wherein the bladder cancer under its superficial form expresses the wild type form of the gene TP53.

20. The method of claim 12, wherein the bladder cancer is a non muscle-invasive bladder cancer.

* * * * *